United States Patent
Janssen

(10) Patent No.: US 11,622,734 B2
(45) Date of Patent: Apr. 11, 2023

(54) METHODS AND SYSTEMS FOR MONITORING COMPLIANCE

(71) Applicant: GE Precision Healthcare LLC, Milwaukee, WI (US)

(72) Inventor: Brian Janssen, Milwaukee, WI (US)

(73) Assignee: GE Precision Healthcare LLC, Milwaukee, WI (US)

(*) Notice: Subject to any disclaimer, the term of this patent is extended or adjusted under 35 U.S.C. 154(b) by 516 days.

(21) Appl. No.: 16/803,233

(22) Filed: Feb. 27, 2020

(65) Prior Publication Data

US 2021/0267555 A1    Sep. 2, 2021

(51) Int. Cl.
*A61B 5/00* (2006.01)
*G16H 40/20* (2018.01)
*G16H 40/63* (2018.01)

(52) U.S. Cl.
CPC .............. *A61B 5/746* (2013.01); *A61B 5/002* (2013.01); *A61B 5/742* (2013.01); *G16H 40/20* (2018.01); *G16H 40/63* (2018.01)

(58) Field of Classification Search
CPC ......... A61B 5/746; A61B 5/002; A61B 5/742; G16H 40/20
See application file for complete search history.

(56) References Cited

U.S. PATENT DOCUMENTS

| | | | |
|---|---|---|---|
| 8,364,250 B2 | 1/2013 | Moon et al. | |
| 9,965,946 B2 | 5/2018 | Al-Ali et al. | |
| 2008/0255880 A1* | 10/2008 | Beller | G06Q 10/00 705/3 |
| 2010/0036676 A1* | 2/2010 | Safdi | G16H 30/20 705/2 |
| 2011/0009710 A1 | 1/2011 | Kroeger et al. | |
| 2018/0075203 A1* | 3/2018 | West | G16H 40/63 |
| 2020/0258624 A1* | 8/2020 | Janssen | G16H 40/20 |

* cited by examiner

*Primary Examiner* — Michael W Kahelin
*Assistant Examiner* — Naveed R. Kolia

(57) ABSTRACT

Various methods and systems are provided for a patient monitoring compliance system. In one embodiment, a method includes determining, over a duration, a relative amount of monitored time where data from the one or more monitoring devices was usable for monitoring one or more parameters of a patient, and if the relative amount of monitored time is less than a threshold amount of monitored time, outputting a first notification.

14 Claims, 12 Drawing Sheets

METHODS AND SYSTEMS FOR MONITORING COMPLIANCE

FIELD

Embodiments of the subject matter disclosed herein relate to medical information systems, and more particularly, to medical patient monitoring.

BACKGROUND

In hospitals and other patient treatment facilities, clinicians often desire to monitor one or more physiological parameters for a given patient as part of care and treatment protocols. For some patient conditions, it may be desirable to provide uninterrupted monitoring for a duration. Additionally, ambulation of the patient is often desirable in order to stimulate patient recovery. To provide uninterrupted monitoring with patient ambulation, clinicians may order telemetry monitoring of a patient, where a portable monitoring device(s) acquiring one or more parameters is coupled to the patient and the monitoring device(s) is configured to measure patient physiological information and other patient health parameters. The monitoring device(s) may transmit patient health data to one or more computing systems located remotely from the patient, where the data may be continuously observed by facility staff for indicators of degradation of the condition of the patients.

BRIEF DESCRIPTION

In one embodiment, a method includes determining, over a duration, a relative amount of monitored time where data from the one or more patient monitoring devices was usable for monitoring one or more parameters of a patient, and if the relative amount of monitored time is less than a threshold amount of monitored time, outputting a first notification. In an additional embodiment, a method includes monitoring the received monitoring device information for a given patient and comparing it with the patient's prescribed monitoring protocol, determining during the monitoring period the compliance of monitoring, and if not in compliance with the monitoring protocol, outputting a first notification.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1A:
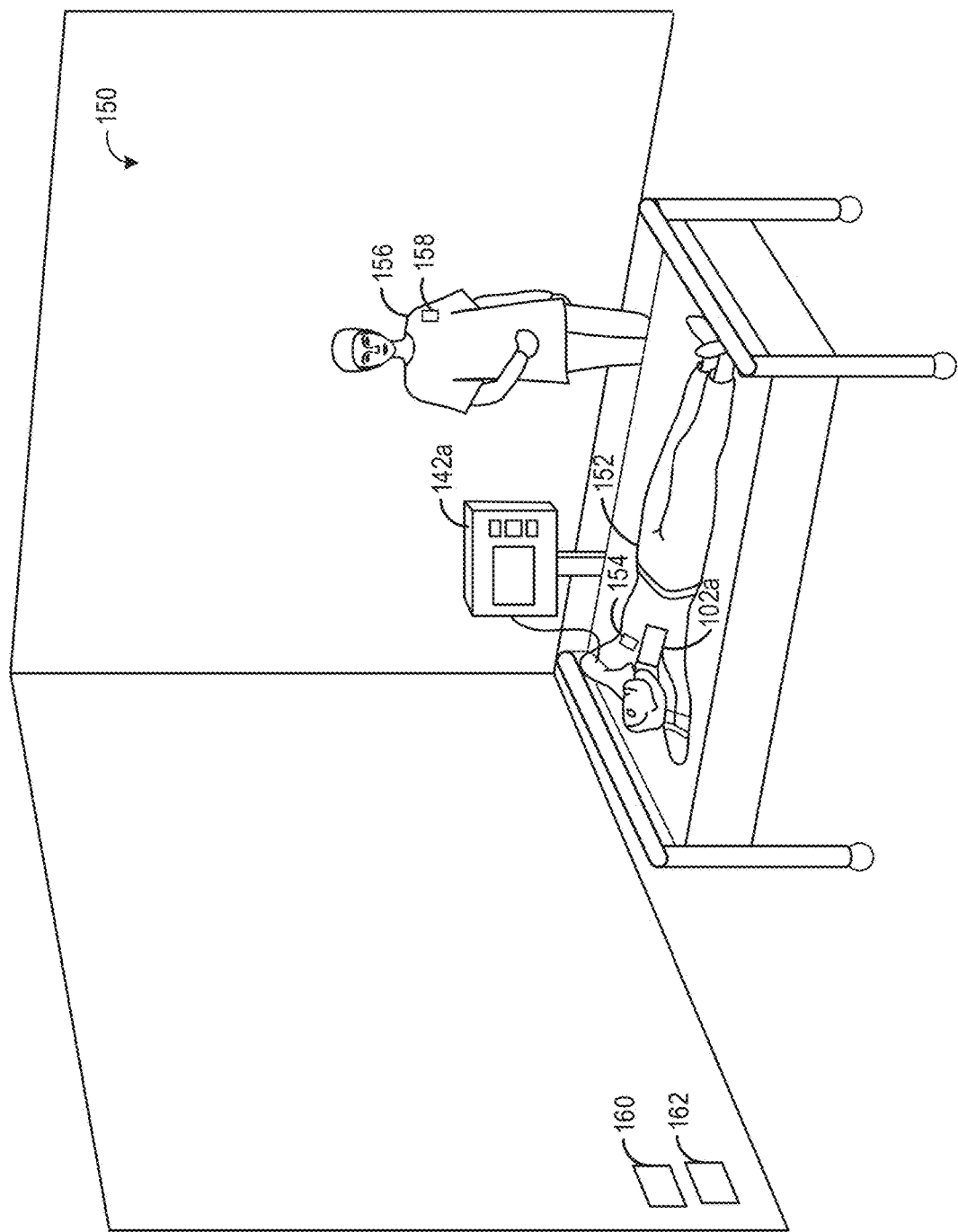
FIG. 1A schematically illustrates an example patient monitoring environment.

The following description relates to various embodiments for a patient monitoring compliance management system. Patient monitoring may include a number of different physiological monitoring devices, sensors, etc. capable of monitoring cardiac, respiratory, neurologic, hemodynamic, pulse oximetry, etc. parameters such as but not limited to electrocardiography (ECG), peripheral capillary oxygen saturation (SpO2), respiration rate, temperature, blood pressures, entropy, blood glucose, and carbon dioxide. Patient monitoring is performed by way of many different forms and approaches with respect to data capture and communication technologies (e.g., hard-wired and wireless networking) and may include monitoring a patient locally (e.g., in-room wired or tethered to a monitor) and/or wirelessly (e.g., in-room, while in transport, ambulating telemetry) In addition to moveable roll stand and room-based semi-fixed or permanently mounted physiological data acquisition equipment acquiring one or more parameters, monitoring may be performed with small, portable devices (whether as multiple separate sensors or as an integrated acquisition device) coupled to the patient in order to enable the patient to ambulate (e.g., walk) remotely relative to a designated hospital bed or treatment room while maintaining monitoring of the condition of the patient (e.g., heart rhythm, oxygenation, and other patient vitals). For example, ambulation of the patient may be desirable for resolution of various medical conditions for which the patient is being treated (e.g., chest pain, syncope, post-surgical). A care provider (e.g., nurse, doctor, or another clinician) may view an output of the monitoring device(s) on the device's user interface, at a remote location such as a patient monitoring central station, via another method such as an Electronic Medical Record system, or at a handheld device throughout the duration that the monitoring device(s) is attached or coupled to the patient.

However, patient monitoring is often not as consistent, timely, nor effective as clinicians would hope. For example, the amount of time from an order being placed to monitor a patient until the patient is actually connected to the monitoring device(s) and being monitored may be unduly long. Further, patients may become unhooked from the device(s) and sensor(s) or otherwise endure lapses in monitoring for periods of time, without clinicians noticing. Thus, while a patient monitoring protocol may dictate 24 hours of continuous and/or non-continuous patient monitoring to diagnose or monitor a given patient condition, due to connection delays, lapses in monitoring, and so forth, actual patient monitoring may be much less than dictated, such as 16 hours rather than 24 hours. Such lapses in patient monitoring degrade the quality and effectiveness of critical patient monitoring activities (e.g., data not captured, missed life critical arrythmia, parameter, and technical alerts) used to support patient care delivery. Additionally, ensuring the correct physiological parameters are monitored for a given patient condition is critical to patient care delivery. Not monitoring a given parameter (i.e., under monitoring) per a given patient diagnosis' or condition's protocol may not provide the care team the appropriate information nor alert them to a changing condition, thereby leading to potential negative outcomes. Conversely, monitoring additional parameters not part of a conditions protocol (i.e., over monitoring), may lead to undue burden on the care team having to hookup/unhook, maintain equipment, and respond to unnecessary technical alerts due to the over monitoring. Besides excess usage of hospital resources, patients may experience discomfort, anxiety, etc. due to the unneeded device equipment connected to them. Overall, little to no methods are currently available to ensure compliance and effective management of patient monitoring protocols.

Thus, according to embodiments disclosed herein, a patient monitoring compliance management system may use smart, automated methods to monitor and notify care teams of non-guideline exceptions and unmonitored time thresholds during monitoring of a patient. Examples include monitoring time to hook-up, unmonitored time (after a patient is hooked up), time to disconnect (once a disconnect order is received), and the under, correct/compliant, or over usage of physiologic parameters per a given protocol. The smart/automated monitoring may be performed on one or more patients in a given hospital or hospital system-wide (i.e., multiple locations) and is in addition to typical machine-based patient monitoring alerts (e.g., an ECG lead(s) comes off, excess artifact due to motion or poor electrode to skin connection, high heart rate, low SpO2, a dysrhythmia). The patient monitoring compliance system may display the monitoring compliance status and alert locally on a device and/or output such information to multiple devices and systems in a more global manner.

The patient monitoring compliance management system described herein may graphically provide a patient list showing patient names, monitored/unmonitored time, parameters monitored (i.e., over-under-correct status with those parameters out of guidelines), and associated alerts in order to improve compliance with patient monitoring protocols. The exemplary patient list is viewable via a display device of the patient monitoring compliance system and other example display devices including but not limited to the monitoring acquisition device, a central station, and Electronic Medical Record system, and/or on a display device of an alert notification system. In some embodiments, the patient list may be viewable via a plurality of computing systems electronically coupled to the patient monitoring compliance system via a network. Thus, care providers may have access to the patient list and may view patient alerts from virtually any allowed location within the medical facility, and even off-site locations in some embodiments.

Figure 1B:
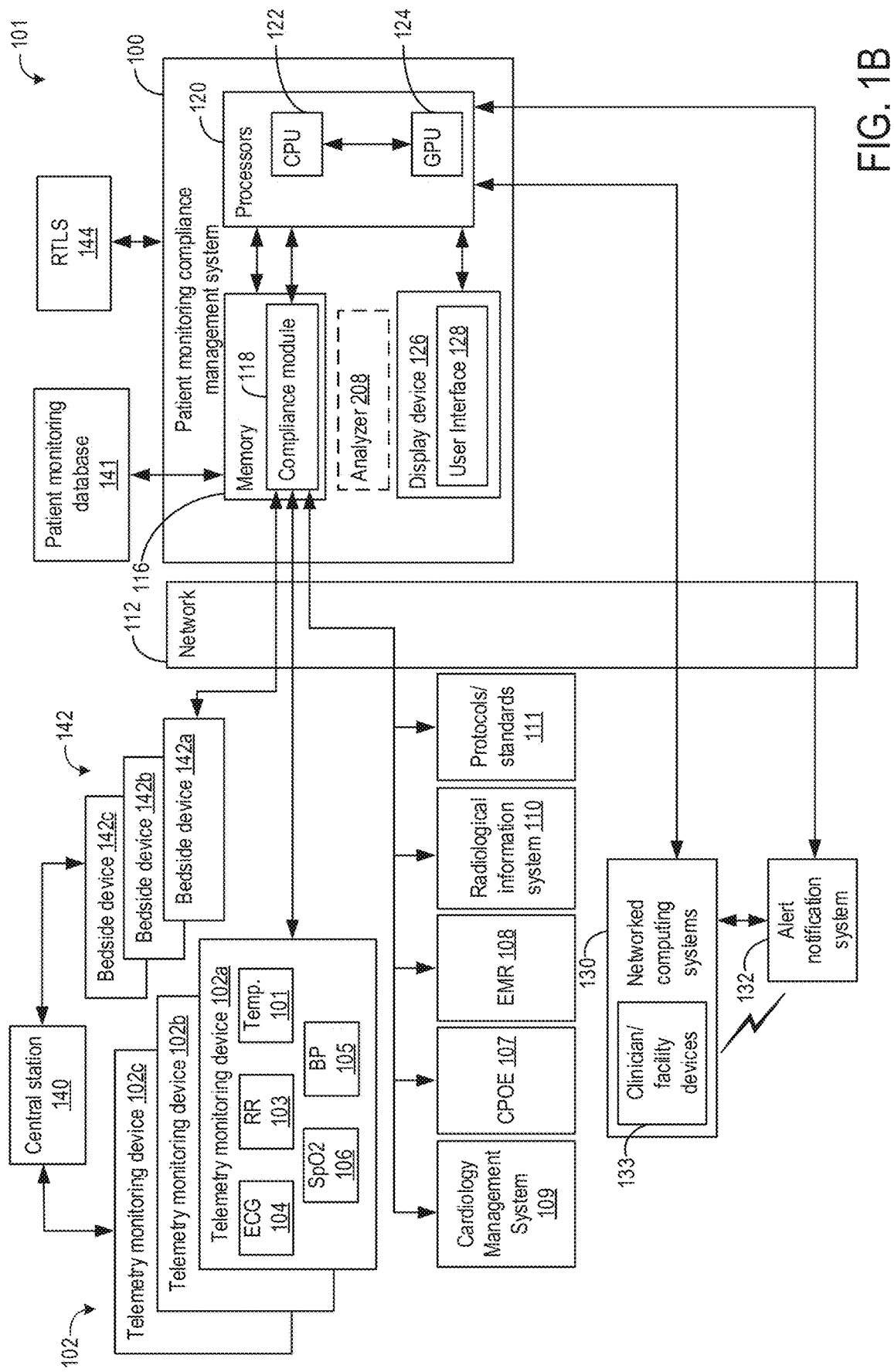
FIG. 1B is a block diagram illustrating a medical information system including a patient monitoring compliance system according to an exemplary embodiment.
Figure 2:
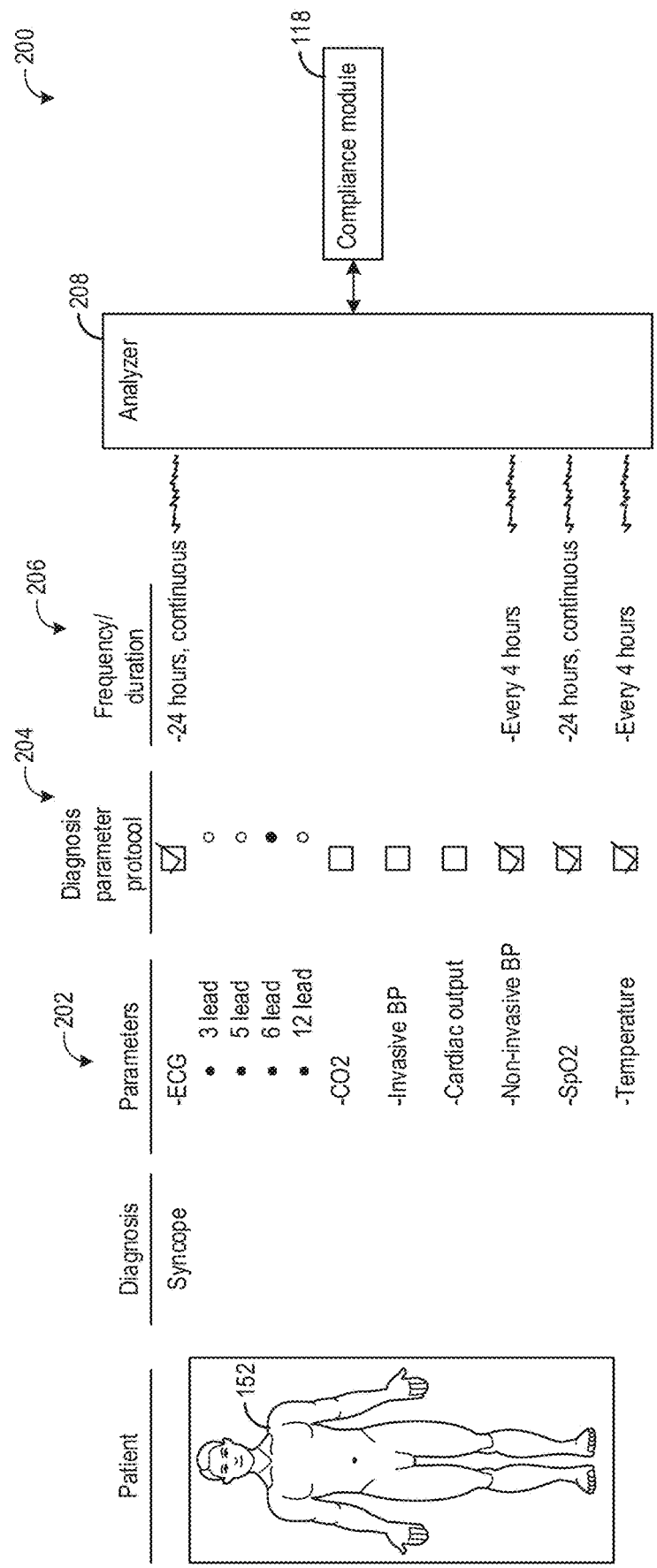
FIG. 2 is a diagram schematically showing a patient monitoring protocol, according to an exemplary embodiment.
Figure 5:
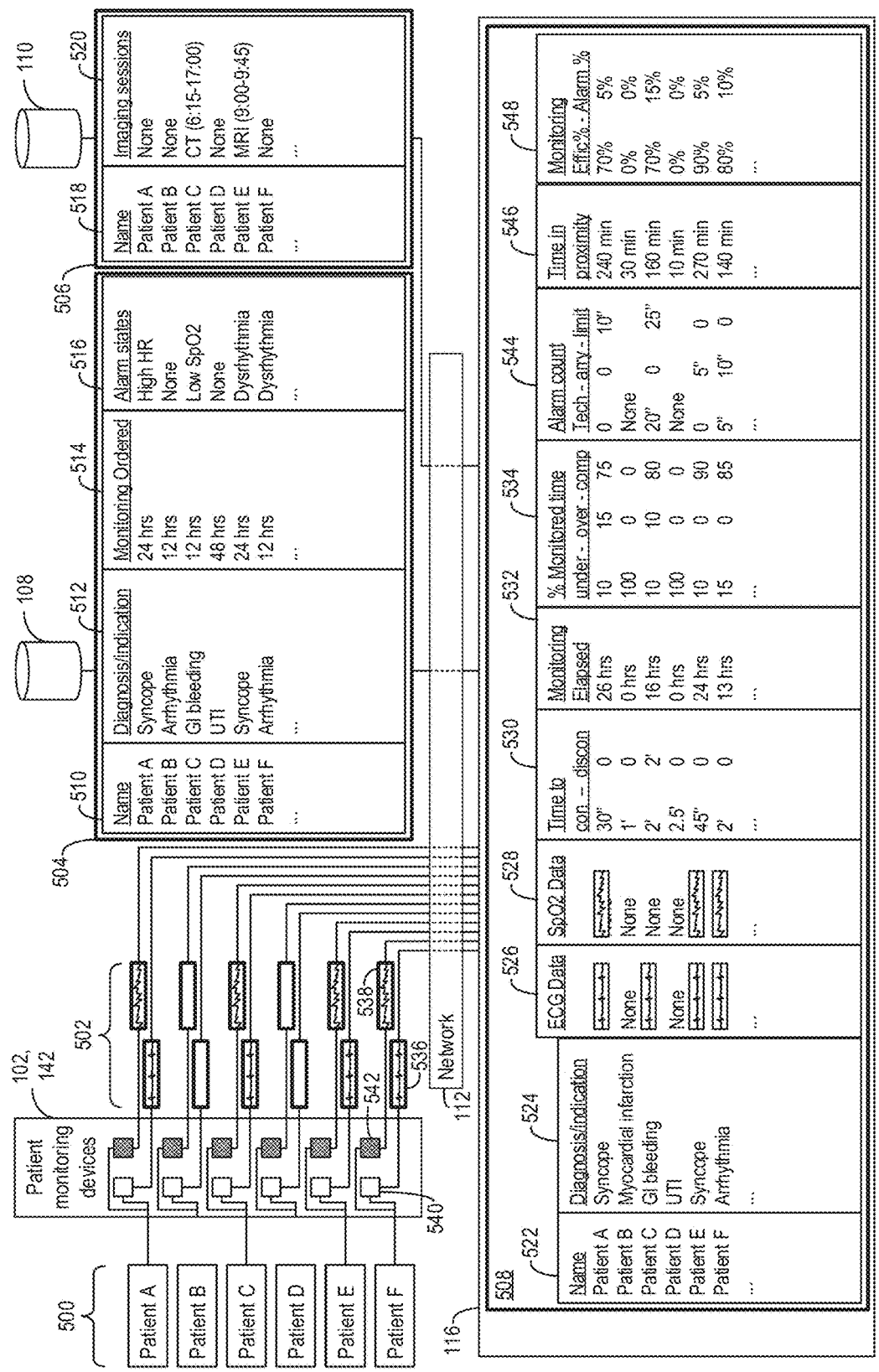
FIG. 5 is a block diagram illustrating acquisition of a patient index including a list of patients and patient information by the patient monitoring compliance system of FIG. 1B, according to an exemplary embodiment.
Figure 6:
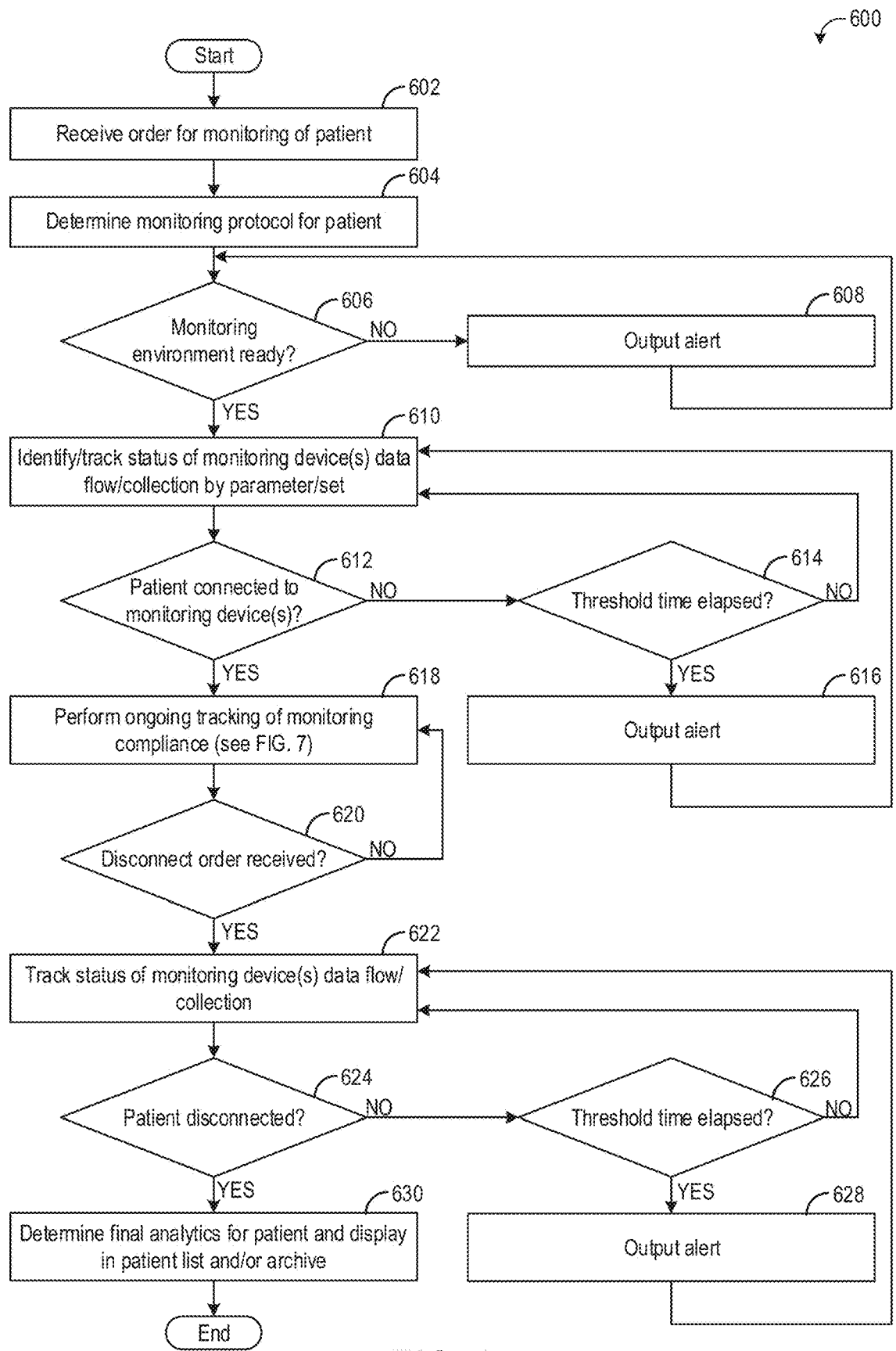
FIG. 6 is a flow chart illustrating a method for monitoring patient monitoring protocol compliance over an episode of patient monitoring via a patient monitoring compliance system, according to an exemplary embodiment.
Figure 7:
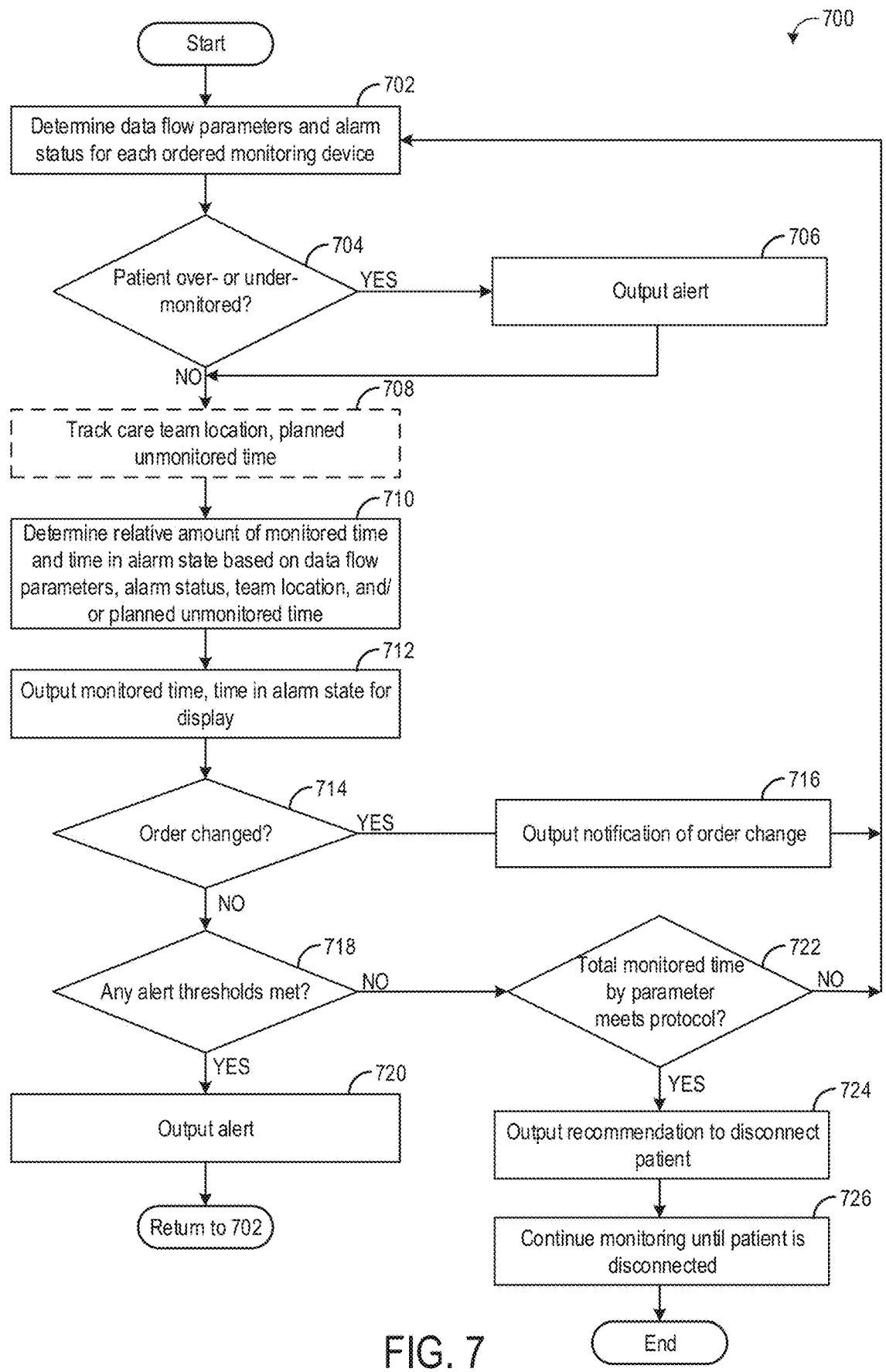
FIG. 7 is a flow chart illustrating a method for monitoring patient monitoring protocol compliance during a monitoring period of an episode of patient monitoring via the patient monitoring compliance system, according to an exemplary embodiment.
Figure 8:
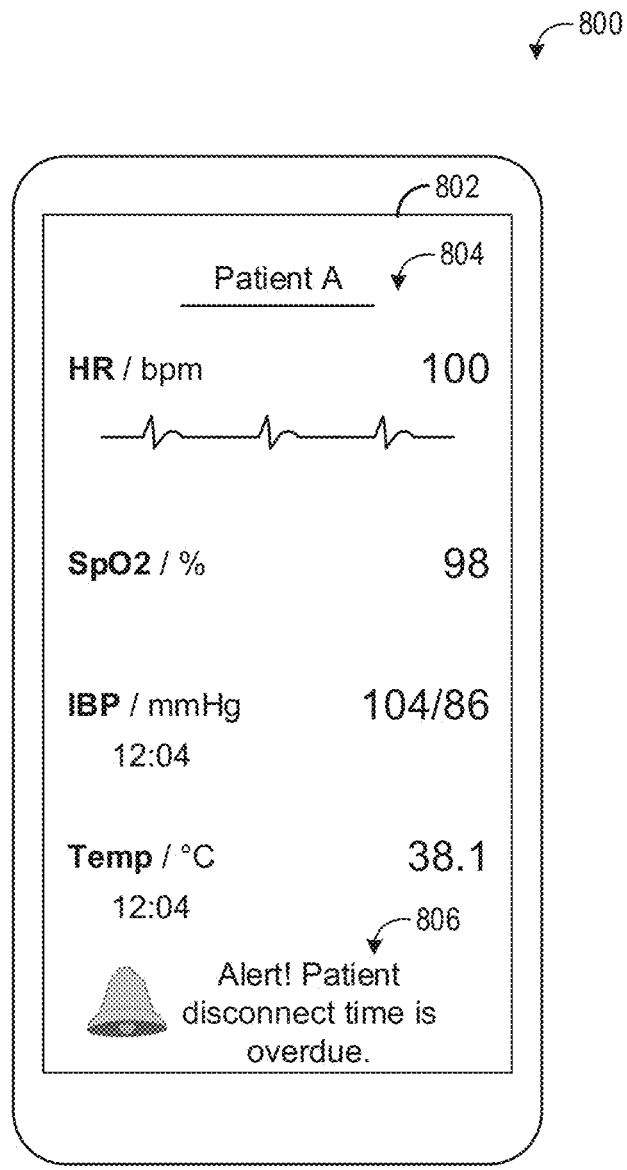
FIG. 8 shows an example graphical user interface (GUI) displayed on a display device, the GUI including an alert generated via the patient monitoring compliance system, according to an exemplary embodiment.

An example patient monitoring environment is shown in FIG. 1A. An example patient monitoring compliance management system is shown in FIG. 1B, which may track monitoring compliance of the patient in FIG. 1A as well as other patients at one or more medical facilities. It should be noted, for simplicity, a single hospital will be referenced, however it is envisioned the system could monitor one or more hospitals' patient monitoring devices. To track patient monitoring compliance for the patient, a monitoring protocol may be obtained or confirmed, and the parameters of the patient monitored by the monitoring devices may compared to the protocol to determine compliance, as shown by the diagram of FIG. 2. Patient monitoring compliance may be tracked over time and various compliance metrics may be determined, as shown by the exemplary timelines of FIGS. 3 and 4. The patient monitoring compliance system may be included in or associated with the medical facility and may be electronically coupled to one or more databases via a network to receive patient information for each admitted patient of the medical facility, as illustrated schematically by FIG. 5. The patient monitoring compliance system may generate a patient list based on the acquired patient information and display the patient list to care providers via a display device, as illustrated in FIG. 5. The patient monitoring compliance system may determine the monitoring status of each patient based on whether a monitoring initiation request or a monitoring cessation request has been ordered and whether patient monitoring data is transmitted to the patient monitoring compliance system, as illustrated by the flowchart of FIG. 6. Additionally, during an on-going patient monitoring session, an amount of unmonitored time and/or time spent in an alarm state, whether an order has changed and subsequently the monitoring protocol is modified, and whether the correct parameters are being monitored per protocol may be tracked and used to issue notifications of patient monitoring status, as shown by the method of FIG. 7. A patient's monitoring status and related notifications may be displayed to one or more users on one or more exemplary devices and systems, as shown in FIGS. 8-10.

FIG. 1A shows an example patient monitoring environment 150, which in the example shown in FIG. 1A is a patient room in a hospital or other medical facility. The exemplary patient monitoring environment 150 may include one or more patient monitoring devices, monitoring one or more physiological parameters. The monitoring environment 150 includes a patient 152 being monitored by a plurality of monitoring devices and also being attended to by a clinician 156. Clinician 156 may be a nurse, physician, medical technologist, or another suitable medical professional. The monitoring devices include a bedside device 142a and a telemetry monitoring device 102a. The monitoring environment 150 depicts the use of more than one monitoring device but it is understood this is non-limiting as the environment 150 could contain one device monitoring one parameter, one device monitoring more than one parameter, multiple devices each monitoring one or more than one parameter, etc. Due to differing patient conditions and the varying patient monitoring needs, one or more devices may be used to support the monitoring needs of the patient and capable of supporting monitoring in various conditions (e.g., in room, in transport, patient ambulation). The one or more bedside devices 142a may be included or mounted in a floor, table top, or roll stand unit that includes one or more leads or other components coupled to the patient or in wireless communication to a device connected to the patient, in order to monitor one or more parameters of the patient (such as ECG, respiration, blood pressure, carbon dioxide levels, etc.). The one or more bedside devices 142a are configured to remain in the patient room, and thus patient 152 may have limited mobility when coupled to the one or more bedside devices 142a.

The telemetry monitoring device(s) 102a may include one or more telemetry devices (with different sensor capabilities) housed in a common unit (as shown) or housed in two or more separate units. The telemetry monitoring device(s) 102a may be positioned on the patient (e.g., via a pouch, holder, or similar, attached to a belt of the patient) or on a movable unit (e.g., a wheeled unit), such that the telemetry monitoring device(s) 102a may leave the patient room if the patient leaves the patient room, and may travel with the patient. The set of telemetry monitoring device(s) 102a may be connected to the patient 152 via one or more leads or other components or in wireless communication with an associated sensor, in order to monitor one or more parameters of the patient (such as ECG, respiration, blood oxygen level, etc.).

The patient monitoring data collected by the monitoring device(s) 142a and 102a may be sent wirelessly (e.g., WiFi, Bluetooth, MBAN) and/or via hard-wired networked connection to one or more associated devices for processing, analysis, storage, display, etc., such as a central station, patient monitoring database, and/or a patient monitoring compliance system, as will be explained in more detail below. The methods of wireless communication by the telemetry monitoring acquisition device and the receiving systems vary widely based on the technology used. In one example communication approach, to facilitate the transfer of the patient monitoring data collected by the telemetry monitoring device(s) 102a, patient monitoring environment 150 and nearby areas (e.g., hallways, closets, open spaces) may include one or more access points 160. Access point 160 may receive and send information (e.g., wirelessly) to telemetry monitoring device 102a (e.g., the patient monitoring data, communication status). The access point sends the received information to a processing server, a central station, a telemetry monitoring system, and/or another suitable device. If patient 152 leaves the patient room and moves throughout the medical facility, patient monitoring data collected by the telemetry monitoring device(s) 102a may be sent to other access points located throughout the medical facility. Patient monitoring data collected by the one or more bedside devices 142a may likewise be sent to a processing and analysis server, the central station, the telemetry monitoring system, and/or another suitable device, via wireless communication with access point 160 or another access point, or via a wired connection. It is understood, this example using a transceiver and access point for data communications is one of many different technologies suitable for sharing acquired patient monitoring data with the associated data processing, analysis, storage, and information viewing system components and infrastructure.

As will be explained in more detail below, when tracking patient monitoring compliance, in-room patient monitoring performed by a clinician may be tracked and included as part of the patient monitoring compliance metrics. It is also envisioned the system capturing and accounting for cases such as when the patient and a care team member(s) are in close proximity to each other (whether in the patient's room or out of room) or the patient is receiving care in an associated support area or unit (e.g., imaging, dialysis, surgery). Thus, at least in some examples, the location of the clinician and/or the patient may be tracked via a real time locating system (RTLS). For example, a first RTLS tag 158 is positioned on clinician 156. First RTLS tag 158 may transmit radiofrequency, optical, and/or ultrasound signals that may be received by receiver 162 in order to track the location of clinician 156 relative to receiver 162. As clinician 156 moves about the patient room and the medical facility, the location of clinician 156 may be tracked via communication between first RTLS tag 158 and other receivers located throughout the medical facility. Receiver 162 (and other receivers in the medical facility) may communicate the location of the clinician to the patient monitoring compliance system. In some examples, patient 152 may also be equipped with a second RTLS tag 154, which may communicate with receiver 162 and/or other receivers in the medical facility to track the location of patient 152 and/or the relative location of the patient 152 to the clinician 156

FIG. 1B schematically shows an example patient monitoring system 101 including a patient monitoring compliance management system 100 that may be implemented in a medical facility such as a hospital. Patient monitoring system 101 may be implemented in the same medical facility as patient monitoring environment 150, and thus some components of patient monitoring environment 150 are included as part of patient monitoring system 101, such as the telemetry monitoring and bedside devices.

Patient monitoring compliance management system 100 includes resources (e.g., memory 116 and processor(s) 120) that may be allocated to store and execute a compliance algorithm for tracking patient monitoring compliance. For example, as shown in FIG. 1B, compliance module 118 is stored within a non-transitory memory of memory 116 of the patient monitoring compliance management system 100 and includes one or more compliance algorithms for tracking patient monitoring device hook-up and disconnect compliance as well as tracking monitoring compliance once the patient monitoring devices are hooked up to actively monitor a patient based on information acquired by the patient monitoring compliance management system 100. As will be described in more detail below, the patient monitoring devices may include telemetry devices (e.g., whereby a patient being monitored by the telemetry devices may ambulate or otherwise move around the medical facility) and/or bedside devices.

Memory 116 includes non-transitory data storage structures, which may include optical memory devices, magnetic memory devices, or solid-state memory devices, for storing programs and routines (e.g., compliance algorithms) executed by processors 120 to carry out various functionalities disclosed herein. Memory 116 may include any desired type of volatile and/or non-volatile memory such as, for example, static random access memory (SRAM), dynamic random access memory (DRAM), flash memory, read-only memory (ROM), etc. Processors 120 may be any suitable processor, processing unit, or microprocessor, for example. In the embodiment shown, processors 120 include central processing unit (CPU) 122 and graphics processing unit (GPU) 124. However, in some embodiments, processors 120 may include only CPU 122 or may include a combination CPU/GPU. In some embodiments, processors 120 may be a multi-processor system, and, thus, may include one or more additional processors (e.g., additional GPUs) that are identical or similar to each other and that are communicatively coupled via an interconnection bus.

Processors 120 are electronically coupled to display device 126 of the patient monitoring compliance management system 100. Display device 126 may be a screen, monitor, mobile/smart device, or other suitable device configured to display an output of the patient monitoring compliance management system 100 to a user (e.g., care provider, monitor technician, system administrator). For example, display device 126 may display a user interface 128 according to an output of processors 120 (e.g., an output of CPU 122, GPU 124, or a combination thereof). User interface 128 may be a text-based interface in some embodiments. In other embodiments, user interface 128 may be a graphical user interface including virtual representations of buttons, icons, and the like, as well as contextual patient information. The patient monitoring compliance management system 100 may further include one or more interface devices (e.g., mouse, keyboard, etc.) that may be utilized by a user of the patient monitoring compliance management system 100 to interact with the user interface 128 of the patient monitoring compliance management system 100 displayed at display device 126. In some embodiments, display device 126 may be a touchscreen configured to respond to a touch of the user in order to enable the user to interact with user interface 128.

As described above, processors 120 may execute compliance instructions (e.g., a stratification algorithm) stored by compliance module 118 and may display an output of the compliance algorithm at the display device 126. For example, the output of the compliance algorithm may be included within user interface 128. The processors 120 may generate a patient list indicating monitoring compliance for each patient (e.g., time to hook-up, percentage unmonitored time, time to disconnect, over-under-correct status with respect to monitored parameter compliance) via the instructions stored by the compliance module 118 based on patient information acquired by the patient monitoring compliance management system 100 from one or more databases, as described further below. The patient monitoring compliance management system 100 may include an analyzer module 208 as described in more detail below with respect to FIG. 2.

The patient monitoring compliance management system 100 may communicate electronically with one or more networked computing systems 130 within and/or external to the facility via network 112. Network 112 may be configured as a wired local area network (LAN), wireless LAN, wide area network (WAN), etc. The networked computing systems 130 may include respective display devices in order to view the stratified patient list generated by the patient monitoring compliance management system 100. Each of the networked computing systems 130 may include a processor, memory, user input device, display (e.g., screen or monitor), and/or other subsystems and may be in the form of a desktop computing device, a laptop computing device, a tablet, a smart phone, or other device. Each of the networked computing systems 130 may be adapted to send and receive encrypted data and display information transmitted by the patient monitoring compliance management system 100, including acquired patient information and the patient list. The networked computing systems 130 may be located locally at the medical facility (such as in a nurse's station or in the room of a patient) and/or remotely from the medical facility (such as a care provider's mobile device).

The patient monitoring compliance management system 100 may be communicatively coupled to one or more systems and databases for acquiring patient information (e.g., patient names, diagnoses, orders, medications, labs, location, etc.). The systems and databases may store and/or control a variety of hospital-, care provider-, and patient-related information, including but not limited to patient admission information (including date of admission and location of the patient within the medical facility), patient care protocols and workflows, and care provider information including which care providers are monitoring/treating which patients. As shown in FIG. 1B, the systems and databases may include (but are not limited to) a cardiology management system 150, a computerized physician order entry (CPOE) system 107, an electronic medical record (EMR) database 108, a radiological information system (RIS) 110, and a protocols/standards system 111. While not shown in FIG. 1B, the systems and databases may further include a laboratory system, a pharmacy system, and/or a document management system. Additional details about the systems and databases will be provided below.

Further, the patient monitoring compliance management system 100 may be communicatively coupled to telemetry monitoring devices 102 and may be configured to receive electronic signals from the telemetry monitoring devices 102. The telemetry monitoring devices 102 may include a plurality of telemetry monitoring devices, with each telemetry monitoring device configured to monitor a different patient. As show, the plurality of telemetry monitoring devices includes a first telemetry monitoring device 102a, a second telemetry monitoring device 102b, and a third telemetry monitoring device 102c. It should be understood that the telemetry monitoring devices 102 may include more or fewer devices than shown in FIG. 1B. Each telemetry monitoring device may include one or more sensors, with each sensor configured to measure a particular patient parameter. For example, the first telemetry monitoring device 102a includes an electrocardiogram (ECG) sensor 104, a peripheral capillary oxygen saturation (SpO2) sensor 106, a respiration rate (RR) sensor 103, a blood pressure (BP) sensor 105, a temperature sensor 101, and/or other sensors. Each telemetry monitoring device (e.g., an ECG sensor, an SpO2 sensor, a blood pressure sensor, a respiration rate sensor, and/or a temperature sensor) may be configured to be connected to a different patient, such that a plurality of patients in the medical facility may be monitored with a respective telemetry monitoring device. The telemetry monitoring devices 102 may send output directly to the patient monitoring compliance management system 100 and/or may send output to the systems and databases (e.g., EMR 108). For example, a telemetry monitoring device monitoring a first patient (e.g., the first telemetry monitoring device 102a) may be configured to send output to the patient monitoring compliance management system 100, and the output acquired by the patient monitoring compliance management system 100 may be processed by the compliance module 118 in order to determine an amount of unmonitored time of the first patient, amount of time in an alarm state for the first patient, and/or other indicators of patient monitoring compliance, which may be used to generate notifications and/or displayed as part of the patient list.

Further still, the patient monitoring compliance management system 100 may be communicatively coupled to a plurality of bedside devices 142 and may be configured to receive electronic signals from the bedside devices 142. The bedside devices 142 may be configured to monitor various patient parameters at the bedside, such that a patient being monitored by the bedside devices may not leave the room in which the bedside devices are located (while still connected to the bedside devices). The bedside devices 142 may include CO2 monitoring devices, invasive blood pressure devices, any of the sensors listed above (e.g., SpO2, temperature, ECG), and/or other devices). Each bedside device may be configured to be coupled to a different patient at the medical facility. Thus, as shown, the bedside devices 142 may include a bedside device 142a in a first patient room, a bedside device 142b in a second patient room, a bedside device 142c in a third patient room, etc. In some examples, the bedside devices 142 may further include therapy devices configured to provide treatment to patients, such as anesthesia machines, infusion pumps, etc. In some examples, the therapy devices may be configured to send electronic signals to the patient monitoring compliance management system 100 indicative of patient status, such as machine settings, patient monitoring parameters, etc. In some embodiments, patient monitoring compliance management system 100 may additionally receive diagnostic imaging information from one or more imaging modalities, such as ultrasound, CAT, MRI, X-ray, etc., via a suitable system/database, such as via RIS 110.

The telemetry monitoring devices 102 and bedside devices 142 may have integrated display devices, such that monitored patient parameters may be displayed in real-time on each device. In other examples, however, one or more of the telemetry monitoring devices and/or the bedside devices may not have an integrated display device. Further, each of the telemetry monitoring devices 102 and each of the bedside devices 142 may be communicatively coupled to one or more central stations 140. Each central station 140 may include a display device via which the patient monitoring parameters monitored by the telemetry monitoring devices and/or bedside devices may be displayed. While the telemetry monitoring devices 102 and bedside devices 142 are shown as communicating with patient monitoring compliance management system 100 via network 112 while patient monitoring database 141 directly communicates with patient monitoring compliance management system 100 and central station 140 directly communicates with the telemetry monitoring devices 102 and bedside devices 142, it is to be appreciated that each of the telemetry monitoring devices 102, bedside devices 142, central station 140, and patient monitoring database 141 may be networked together with patient monitoring compliance management system 100 (e.g., via network 112 or another network).

The patient monitoring compliance management system 100 may determine an amount of unmonitored time and correspondingly an amount of monitored time for each patient undergoing monitoring via the compliance module 118 based on the information acquired by the patient monitoring compliance management system 100 (e.g., telemetry sensor data from telemetry monitoring sensors 102, bedside monitoring data from bedside devices 142). In some examples, the amount of unmonitored time may be adjusted to account for planned unmonitored time (e.g., while the patient is undergoing diagnostic imaging) and/or to account for times when the patient is not undergoing telemetry or bedside monitoring but is being "monitored" in-person by one or more care providers. This additional information indicative of the planned unmonitored time and in-person care may be obtained from the systems and databases described above (e.g., EMR 108, RIS 110, and/or cardiology management system 150) and/or other information sources.

For example, a real-time locating system (RTLS) 144 may be configured to track clinician/care provider location relative to each monitored patient. If a clinician is within a threshold distance of a patient, that patient may considered to be monitored by that clinician. The RTLS 144 may include a plurality of RTLS tags, with each tag coupled to a respective clinician or patient. The RTLS 144 may further include a plurality of receivers, with each receiver located in a different location of the medical facility and each receiver configured to detect signals sent by the RTLS tags, when the RTLS tags are within vicinity of the receiver. Each receiver may send location information for each nearby tag to the patient monitoring compliance management system 100, thereby allowing the patient monitoring compliance management system 100 to track clinician and patient location.

In some embodiments, the systems and databases may be external databases accessible by the patient monitoring compliance management system 100 via a secured hospital interface (e.g., network 112). In other embodiments, the systems and databases may be local databases (e.g., housed on the patient monitoring compliance management system 100). The systems and databases may include patient information (e.g., patient names, diagnoses, etc.) stored in mass storage device(s) configured to communicate with secure channels (e.g., HTTPS and TLS), and store data in encrypted form. The EMR database 108 may be configured to control access to patient electronic medical records such that only authorized healthcare providers may edit the electronic medical records. An EMR for a patient may include patient demographic information, family medical history, medical history, lifestyle information, preexisting medical conditions, past and current medications, past and current lab test results, allergies, surgical history, past medical screenings and procedures, past hospitalizations and visits, etc.

Cardiology management system (CMS) 150 may collect, store, analyze, and/or manage information from medical devices (e.g., resting ECG, stress or exercise ECG, Holter ECG, patient monitoring, etc., medical devices) used to detect and diagnose cardiac-related issues of patients. In some examples, cardiology management system 150 may interface with EMR 108 in order to update patient electronic medical records to indicate the detected and/or diagnosed cardiac-related issues. In some examples, while in the ED, a suspected myocardial infarction patient could have a resting ECG performed on them. If the device and CMS detects an abnormality, this could be an indication to the physician that patient monitoring should be considered to be administered or is part of the guideline or protocol to be followed.

CPOE system 107 may receive orders from care providers and communicate the orders to other care providers or department devices responsible for fulfilling the orders. The orders may include instructions for the treatment of patients, such as procedures to be performed, medications to be administered, operational sequences to be followed, and the like. Thus, when a clinician determines that a patient is to undergo monitoring or be removed from monitoring, the patient monitoring compliance management system 100 may be informed of the order to connect the patient to the telemetry monitoring sensors and/or bedside devices or the order to remove the patient from the telemetry monitoring sensors and/or the bedside devices via the CPOE system 107.

Radiological information system (RIS) 110 may include one or more computing devices associated with one or more on-site or off-site diagnostic/medical imaging systems that obtain medical images of patients as ordered by the care provider(s). The one or more computing devices may include resources (e.g., memory and processors) allocated to manage various aspects of the radiological procedures, such as patient scheduling, patient tracking, results transmission, and the like.

In some examples, the patient monitoring compliance management system 100 may interface with one or more other databases, such as patient monitoring database 141, for on-going data processing, data storage, analytics, reporting, etc. In the embodiment shown, database 141 is a database located within the patient facility. However, in other embodiments, the database 141 may utilize a cloud-based data architecture and may not be located within the patient facility.

Patient monitoring compliance management system 100 may periodically query the systems and databases described herein (e.g., cardiology management system 150, CPOE 107, EMR 108, RIS 110, and protocols/standards system 111) to acquire updated information (e.g., patient information, protocols, etc.) for managing (e.g., forming, updating, etc.) the patient list and/or issuing notifications.

The patient monitoring compliance management system 100 may integrate data from the telemetry monitoring devices 102 (e.g., data generated by the telemetry monitoring devices 102), bedside devices 142, and the systems and databases via the compliance module 118 to enable smart, automated management of monitoring of the patients within the facility. The compliance module tracks patient monitoring protocol compliance for a plurality of patients, with the compliance including time to connect metrics (e.g., before the patient is connected to the monitoring devices but after an order has been placed), monitoring metrics (e.g., unmonitored time, time in alarm state, correctness of monitored parameters per guidelines or protocol), and disconnect metrics (e.g., before the patient is disconnected from the monitoring devices but after an order has been placed) based on the patient information acquired from the systems and databases in combination with output received by the telemetry monitoring devices 102 and bedside devices 142.

Protocols/standards system 111 may store patient monitoring protocols or standards for a plurality of different patient conditions or indications. The monitoring protocols or standards may indicate, for each of a plurality of indications, how long a patient presenting with that indication is to be monitored, what physiological parameters should be monitored, what potential diagnoses or treatments may be associated with different monitoring outcomes, what telemetry and/or bedside devices should be used to monitor a patient having a given indication, and so forth. For example, if a patient is admitted to a medical facility with an indication of syncope, the patient monitoring compliance management system 100 may retrieve monitoring guidelines for patients presenting with syncope, which may dictate which parameters should be measured, how long the patient is to be monitored for each parameter, and with which telemetry and/or bedside monitoring devices. The patient monitoring compliance system may then compare the amount of time the patient has been monitored to the recommended amount of monitoring time and issue notifications based on the elapsed versus recommended time. The system may also monitor which parameters are being collected with respect to the protocol/guidelines and issue notifications based on whether the patient is being under monitored (i.e., missing one or more parameters) or over monitored (i.e., monitoring a parameter not needed).

In some embodiments, a separate alert notification system 132 may communicate with patient monitoring compliance management system 100 via network 112 (or other suitable connection). The alert notification system 132 may include resources (e.g., memory and one or more processors) allocated to distributing alerts generated by patient monitoring compliance management system 100. For example, while patient monitoring compliance management system 100 may include a display device 126 for displaying the alerts described herein, care provider interaction with the display device 126 may be limited. Thus, to ensure the alerts generated by the patient monitoring compliance management system 100 are distributed to all relevant care providers, the alert notification system 132 may push alerts to the appropriate devices of the networked computing systems 130, which may include clinician/facility devices 133 (e.g., smart devices, pagers, alarm boards, phones, monitoring technician workstations) and associated monitoring devices such as central stations 140, telemetry monitoring devices 102, and bedside devices 142. Further, the alert notification system 132 may include its own display device on which alerts may be displayed.

As used herein, the terms "device" "sensor," "system," "unit," or "module" may include a hardware and/or software system that operates to perform one or more functions. For example, a device, sensor, module, unit, or system may include a computer processor, controller, or other logic-based device that performs operations based on instructions stored on a tangible and non-transitory computer readable storage medium, such as a computer memory. Alternatively, a device, sensor, module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "devices," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, patient monitoring compliance management system 100 is shown in FIG. 1B as constituting a single entity, but it is to be understood that patient monitoring compliance management system 100 may be distributed across multiple devices, such as across multiple servers, with at least one of the servers including the compliance module 118.

While not specifically shown in FIG. 1B, additional devices described herein (CPOE system 107, EMR database 108, RIS 110, protocols/standards system 111, cardiology management system 150, and networked computing systems 130) may likewise include user input devices, display devices, memory, and processors similar to communication memory 116, processors 120, and display device 126 described above, and thus the description of memory 116, processors 120, and display device 126 likewise applies to the other devices described herein. As an example, the networked computing systems 130 may store user interface templates in memory that include placeholders for relevant information stored and output by patient monitoring compliance management system 100. For example, one or more of networked computing systems 130 may store a user interface that displays the patient list output by the patient monitoring compliance management system 100. The user input devices of the networked computing systems 130 may include keyboards, mice, touch screens, microphones, or other suitable devices.

FIG. 2 shows an example diagram 200 schematically illustrating an exemplary patient monitoring protocol for monitoring a patient according to an embodiment of the disclosure. When a patient is being treated at a medical facility, based on patient symptoms, clinical diagnosis, clinician judgement, and/or other reasons, the patient may be monitored with one or more monitoring devices. To determine which parameters should be monitored and potentially which monitoring devices should be used to monitor the patient, and for how long, a patient monitoring protocol may be applied. The patient monitoring protocol may be specific to a diagnosed or suspected patient condition, and in some examples may further be based on patient information (e.g., age, height/weight, sex, etc.). The patient monitoring protocol could be based on hospital-specific guidelines, follow accepted peer-reviewed published guidelines, or a combination thereof. It is envisioned, the protocols would be setup and configured in the protocols/standards system 111. Once a patient monitoring protocol is selected for the patient, the patient monitoring parameters and devices specified by the selected monitoring protocol may be ordered to be connected to the patient, and the patient may be monitored for the duration(s) specified by the protocol. The patient parameters monitored by the monitoring devices may be sent to the patient monitoring compliance system for compliance monitoring, as explained herein.

Thus, as shown in FIG. 2, patient 152 may be a candidate for patient monitoring based on a suspected or diagnosed condition of the patient, herein syncope. One or more patient parameters of patient 152 may be monitored via one or more monitoring devices. The one or more patient parameters may be selected from among a plurality of possible parameters 202 based on the applicable/selected patient monitoring protocol, thereby generating a diagnosis parameter protocol 204 that dictates which parameters are to be monitored. The plurality of possible parameters 202 shown in FIG. 2 include ECG (with a choice of 3, 5, 6, or 12 lead ECG), CO2, invasive blood pressure (IBP), cardiac output, non-invasive blood pressure (NIBP), SpO2, and temperature. However, other patient monitored parameters are possible.

A frequency/duration 206 for monitored parameter may also be established. In some examples, one or more of the possible parameters may be non-continuous. For example, the NIBP and temperature may be non-continuous, such that measurements of each non-continuous parameter are only performed at specified time intervals, such as once an hour, once every four hours, etc. Continuously monitored parameters (e.g., ECG, SpO2) may be measured as frequently as the sensor/device is configured to measure (e.g., each time that device is capable of taking a measurement, a measurement is taken).

The patient monitoring protocol 204 may be selected from a plurality of monitoring protocols. For example, the patient monitoring protocol 204 may be selected from the protocols/standards system 111 of FIG. 1B based on the diagnosis of the patient (e.g., syncope). The selected patient monitoring protocol may indicate that the parameters of patient 152 that should be monitored include a 6 lead ECG, SpO2, NIBP, and temperature. Further, the selected patient monitoring protocol may indicate a duration and frequency that each parameter is to be monitored, such as an episodic measurement every four hours for NIBP and temperature and 24 hours of continuous monitoring for ECG and SpO2.

The patient may then be monitored by one or more monitoring devices according to the patient monitoring protocol. For example, patient 152 may be monitored with an ECG sensor, an NIBP sensor, an SpO2 sensor, and a temperature sensor. While the monitoring device/sensor is collecting and processing collected patient information, the measured parameter data, alert information, etc. is sent to an analyzer module 208. Analyzer module 208 may be an on-going processing and analysis module within the patient monitoring compliance management system 100. The analyzer module 208 may collect, aggregate, summarize, and/or analyze patient monitoring data in order to determine monitoring compliancy. Non-limiting examples of patient monitoring data that may be collected, aggregated, summarized, and/or analyzed via the analyzer module 208 to determine monitoring compliancy are provided herein below. The examples provided below and throughout the present disclosure are illustrative of how the analyzer module 208 and/or compliance module 118 may collect, aggregate, summarize, and/or analyze patient monitoring data to determine monitoring compliance. For example, as shown, ECG data, NIBP data, SpO2 data, and temperature data are sent to the analyzer module 208. The analyzer module 208 monitors and summarizes the status of each parameter during a monitoring session, and thus receives the patient monitoring data (e.g., from the ECR sensor, NIBP sensor, SpO2 sensor, and temperature sensor). The analyzer module 208 continuously analyzes, aggregates, and summarizes the patient monitoring data to determine a number of factors such as but not limited to each parameter's data collection initiation time and duration, clinical and technical alarm states and durations, etc. (e.g., whether any of the sensors/devices are in a threshold based alarm state and for how long), determine if any of the sensors are not currently monitoring the patient due to the sensors/devices being disconnected from the patient, ascertain whether offline (e.g., not communicating with the analyzer), etc. The analyzer module 208 may be part of the management system 100 and/or part of the compliance module 118 or may work with the compliance module 118 to track patient monitoring compliance, as explained below.

Figure 3:
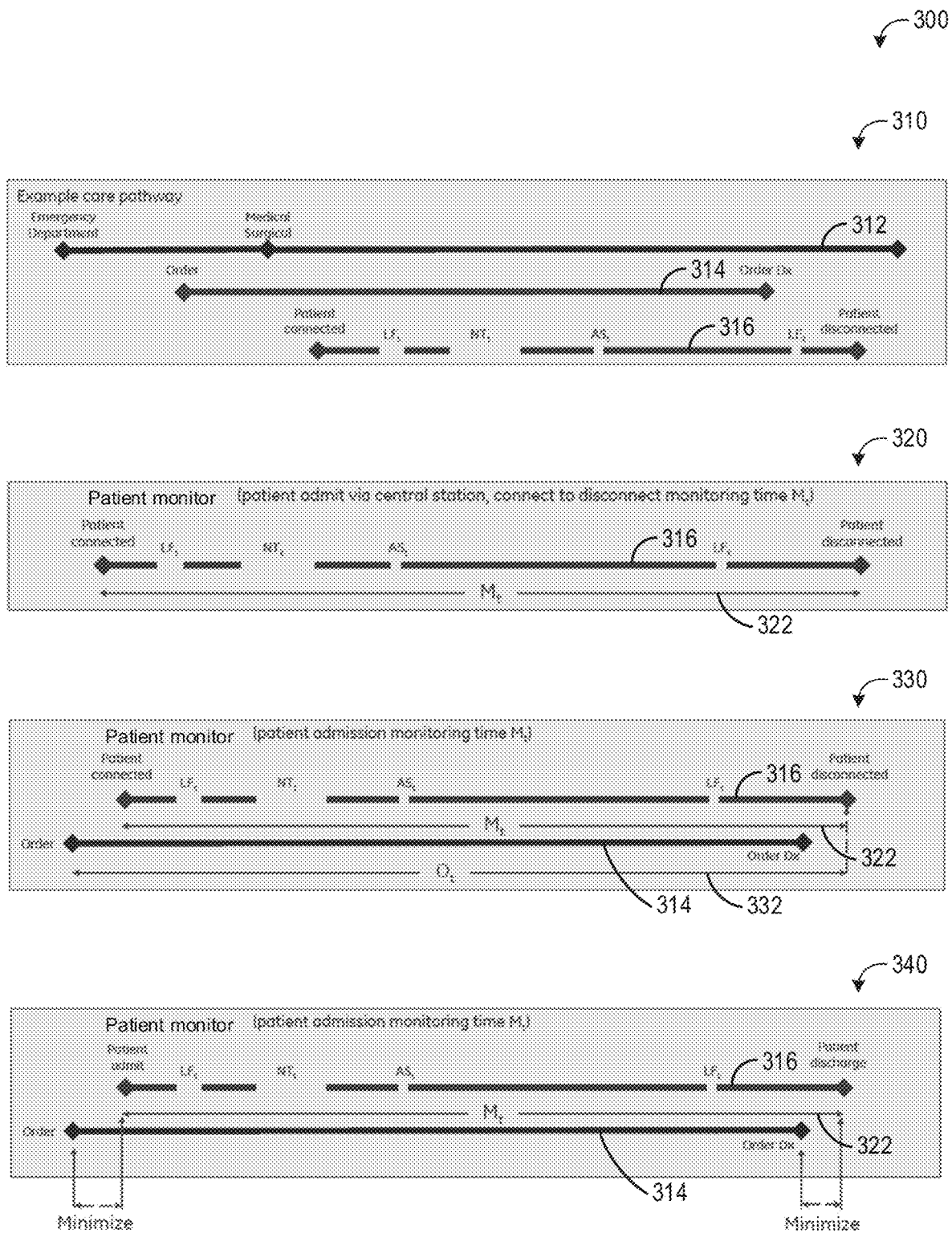
FIG. 3 shows a set of example timelines of monitoring compliance metrics, according to an exemplary embodiment.

FIG. 3 shows sets of timelines 300 each depicting various ways in which patient monitoring compliance may be quantified for a patient at a medical facility. A first set of timelines 310 includes a patient admission timeline 312, a monitoring order timeline 314, and an actual patient monitoring timeline 316. The patient admission timeline 312 may extend from an admission time point (shown by a diamond at the beginning of timeline 312) where the patient was admitted to the emergency department of the medical facility to a discharge time point (shown by the diamond at the end of timeline 312) where the patient was discharged from the medical facility. The monitoring order timeline 314 extends from a connect order time point (the diamond at the beginning of timeline 314) when an order for patient monitoring was placed (e.g., by a clinician attending to the patient) to a disconnect order time point (the diamond at the end of timeline 314) when an order for disconnecting the patient (thus terminating patient monitoring) was placed.

The actual patient monitoring timeline 316 shows the time frame during which the patient was actually monitored by a monitoring device. The actual patient monitoring timeline 316 starts at a connect time point (the diamond at the beginning of the timeline 316, labeled "patient connected") where the patient was actually connected to the monitoring device and extends, non-continuously, until a disconnect time point (the diamond at the end of the timeline 316, labeled "patient disconnected") where the patient was actually disconnected from the monitoring device. The actual patient monitoring timeline 316 includes gaps where the patient was not monitored by the monitoring device. A first gap in patient monitoring is shown as being due to lead failure, where the lead connecting the patient to the monitoring device fell off or otherwise stopped collecting patient monitoring data for a duration referred to as LFt. A second gap in patient monitoring is shown as being due to no telemetry, where the patient was out of range of any access points capable of receiving the data transmitted from the monitoring device for a duration referred to as NTt. A third gap in patient monitoring is shown as being due to an arrhythmia suspend, where the patient monitoring data collection is suspended for a duration referred to as ASt because the ECG arrhythmia detection algorithm was unable to process and analyze the collected data due to excessive artifact. A fourth gap in patient monitoring is shown as also being due to lead failure for a duration (again LFt). Other types of monitoring gaps may be detected and monitored, such as signal artifacts that render the patient monitoring data unusable for reliably monitoring the patient parameter. Though not shown in 316 for simplification purposes but covered in subsequent sections, other reasons for unmonitored time (e.g., diagnostic imaging sessions, personal hygiene events, planned clinical events in the presence of care givers) are envisioned to be determined and accounted for in arriving at effective device and patient monitoring times and alert thresholds.

By comparing the timelines in the first set of timelines 310, various compliance metrics may be determined, such as a percentage of the patient stay at the medical facility where the patient was monitored (e.g., by comparing timeline 316 to timeline 312), a percentage of ordered time that the patient was monitored (by comparing timeline 316 to timeline 314), a percentage of effective monitoring time (by determining how much of timeline 316 was spent in an actual monitoring state by subtracting each LFt, NTt, and ASt from the overall time from the connect time point to the disconnect time point), and/or a time delay in hook-up or disconnect (by comparing when the order was placed to when the patient was connected and by comparing when the disconnect order was placed until the patient was disconnected).

While not shown the first set of timelines 310, alarm states of the monitoring device may be tracked, and a total percentage of time in alarm while being monitored may be determined. The alarms may be physiological alarms, such as threshold/limit based alarms (e.g., a value of the patient monitoring data measured by the monitoring device over or below a threshold value) or arrhythmia alarms (e.g., ventricular tachycardia, pause). The alarms may be technical or processing alarms, such as leads off, out of range, signal quality and/or signal strength based alarms.

A second set of timelines 320 includes the actual patient monitoring timeline 316 and a total monitoring timeline 322. The total monitoring timeline 322 shows a duration (Mt) starting when the patient was connected and ending with the patient was disconnected. The timeline 316 and timeline 322 may be compared to determine an exemplary effective device monitoring time, which may be calculated based on the following equation:

$$\text{Effective device monitoring time} = M_t - \Sigma LF_t - \Sigma AS_t - \Sigma NT_t / M_t$$

A third set of timelines 330 includes the monitoring order timeline 314, the actual patient monitoring timeline 316, the total monitoring timeline 322, and an order to disconnect timeline 332. The order to disconnect timeline 332 shows a duration (Ot) starting when the patient was ordered to be connected and ending with the patient was disconnected. The timelines may be compared to determine an exemplary effective patient monitoring time, which may be calculated based on the following equation:

$$\text{Effective patient monitoring time} = M_t - \Sigma LF_t - \Sigma AS_t - \Sigma NT_t / O_t$$

A fourth set of timelines 340 includes the monitoring order timeline 314, the actual patient monitoring timeline 316, and the total monitoring timeline 322. The fourth set of timelines 340 may be compared to identify hook-up and disconnect delays to be minimized. The hook-up delay may be the amount of time that elapses from when the order to monitor the patient is entered to when the patient is actually connected to the monitoring device. The disconnect delay may be the amount of time that elapses from when the order to disconnect the patient is entered to when the patient is actually disconnected. By tracking monitoring compliance, including the hook-up and disconnect delays, actions may be taken to minimize the delays, thereby maximizing the actual monitored "prescribed" monitoring time, increasing patient safety and improving equipment utilization and patient throughput.

Figure 4:
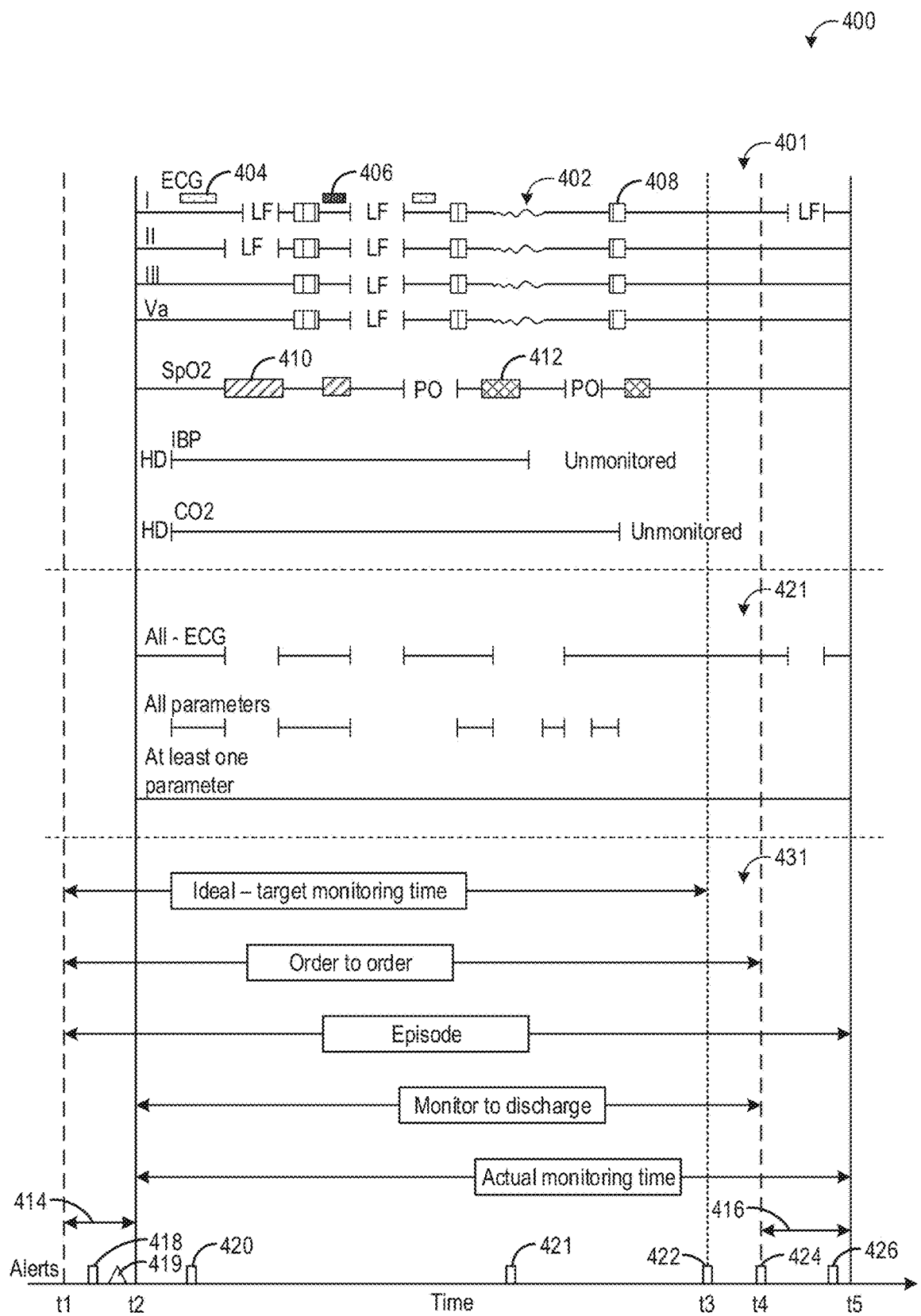
FIG. 4 is an example timeline showing a patient monitoring data acquisition and events over the course of an episode of patient monitoring, according to an exemplary embodiment.

FIG. 4 shows an example timeline 400 of monitoring events for a patient undergoing monitoring according to the methods disclosed herein. The monitoring events illustrated in the timeline 400 includes a first set of plots 401 showing monitoring device status, a second set of plots 421 showing various representations of monitored time for the patient, and a third set of plots 431 showing total monitoring time durations. All of the plots illustrated in timeline 400 are depicted as a function of time (plotted on the horizontal, x-axis). Timeline 400 further includes a set of alerts shown along the bottom of the timeline. Time points of interest are marked along the x-axis. As shown, a first time point (t1) indicates when a patient monitoring order was received for the patient, a second time point (t2) indicates when the patient was actually connected to at least one monitoring device, a third time point (t3) indicates when the patient monitoring compliance system determined that the recommended guidelines for how long to monitor the patient had been met, a fourth time point (t4) indicates when an order to disconnect the patient was entered, and a fifth time point (t5) indicates when the patient was actually disconnected.

The first set of plots 401 includes a set of ECG plots, including plots for four ECG leads (I, II, III, and Va), an SpO2 plot, a blood pressure plot (IBP), and a CO2 plot. The IBP and CO2 devices may be included as bedside devices while the ECG and SpO2 may be telemetry devices or all the parameters may be collected by a single bedside monitor, at least in some examples. Interruptions in the data signals output by the monitoring device(s) are shown for each plot. A lead failure, represented by LF, indicates a period where a lead (or probe or other portion of the monitoring device) was not attached to the patient or was otherwise unable to acquire patient monitoring data. A probe off period, represented by PO, indicates a period where a probe was removed, whether intentionally (e.g., for diagnostic imaging) or unintentionally. No telemetry, which is not shown in FIG. 4, indicates a period where the patient is out of transmission range, loss of multiple leads or ground lead, dead battery, networking/communication issues, etc., and thus any patient monitoring data collected by the monitoring devices is not received by the patient monitoring compliance system or any other downstream device. The wavy portion of the plots, indicated generally at 402, indicates signal artifacts present in the signals from the monitoring devices. A hook-up delay, represented as HD, indicates that the monitoring device was not connected when ordered. For example, a clinician may have connected the ECG sensor (including the four leads) and SpO2 sensor but forgot or did not have the equipment on hand to get the IBP monitoring device connected, and thus had to procure the equipment, resulting in a hook-up delay.

Thus, for the exemplary set of ECG plots, the I lead exhibited three lead failures, the II lead exhibited two lead failures, and both of the III and Va leads exhibited a period of lead failure (a period of lead failure for all the ECG leads overlaps). Further, each ECG lead exhibited a period of signal artifact at 402.

For the remaining monitoring device status plots, the SpO2 probe exhibited two periods of probe/sensor off and the CO2 probe had a hook-up delay and an unmonitored period. The unmonitored period may include a period where the CO2 probe was disconnected from the patient, whether due to the patient monitoring protocol indicating a shorter duration of CO2 monitoring (and thus the removal of the CO2 probe was appropriate) or due to clinician error. The IBP probe, while connected at the same time as the CO2 probe, may not be included in the patient monitoring protocol and thus the presence of the IBP monitoring may be in error and may represent an over-monitored parameter.

Various times in alarm states are also shown on the first set of plots 401. A high heart rate alarm period 404 is shown, determined based on the ECG output, occurring at two time points, where patient heart rate was above a first threshold heart rate. A low heart rate alarm period 406 is shown determined based on the ECG output, occurring at one time point, where patient heart rate was below a second threshold heart rate. Additional alarms are shown for the ECG parameter, including a dysrhythmia event (e.g., as shown by 408) such as atrial fibrillation, pause, etc., as determined by the ECG processing system and alerted to the care team as well as the patient monitoring compliance management system. Two alarms are shown for the SpO2 parameter, including a high SpO2 alarm 410 (where patient SpO2 is above a first threshold SpO2) and a low SpO2 alarm 412 (where patient SpO2 is below a second threshold SpO2). As shown in FIG. 4, the high SpO2 alarm occurred at two time points and the low SpO2 alarm occurred at two time points.

The second set of plots 421 illustrates different ways in which the monitoring parameter statuses may be aggregated for presentation to a user such as a clinician or administrator. The first plot shown in the second set of plots 421 (the "All—ECG" plot) is a plot showing monitored time for all the ECG leads. As appreciated from the "All—ECG" plot, four separate periods where at least one ECG lead was not monitoring the patient occurred over the duration of patient monitoring (e.g., from t2 to t5). The actual amount of time where ECG was monitored may be 20 hours, which is less than the 27 hours of actual monitoring time (described below). The second plot shown in the second set of plots 421 (the "All parameters" plot) is a plot showing monitored time for all monitoring parameters as dictated by the patient monitoring protocol. Thus, because the IBP parameter was not dictated by the monitoring protocol, the presence or absence of IBP monitoring is not tracked when determining the all parameters monitoring time. As appreciated from the "All parameters" plot, six separate periods where at least one monitoring parameter was not being monitored for the patient occurred over the duration of patient monitoring (e.g., from t2 to t5). Some of the unmonitored periods were relatively long and resulted in more unmonitored time than monitored time. For example, the time that all parameters were monitored may be 9 hours, over a total monitored duration of 27 hours. Thus, for this patient, overall monitoring was not effective, given that more often than not, the patient was not being monitored for all of the parameters by the monitoring device(s). The third plot shown in the second set of plots 421 (the "At least one parameter" plot) is a plot showing time where at least one parameter was monitored for the patient. As appreciated from the "At least one parameter" plot, at least one monitoring device was monitoring the patient over the duration of patient monitoring (e.g., from t2 to t5).

Thus, the second set of plots 421 shows that different ways of compiling the amount of monitored time may result in different indications of monitoring compliance. For example, by calculating time where at least one monitoring parameter indicated in the monitoring protocol is being monitored, monitoring compliance is shown as being high. However, by calculating time where all monitoring parameters indicated by the monitoring protocol are being monitored, monitoring compliance is shown as being low. The relative amount of monitored time described above with respect to FIG. 3 may be calculated for each monitored parameter individually (such as shown for the ECG plot), for all monitored parameters together where any unmonitored time is calculated (as shown for the all parameters plot), and/or for all monitored parameters together where only overlapping unmonitored time for all parameters is calculated (as shown for the at least one parameter plot), as each way of aggregating the monitored time may be informative for different reasons.

The third set of plots 431 shows different durations of patient monitoring time. The first plot in the third set of plots 431 shows an ideal monitoring time for the patient, commencing at time t1 when order to monitor the patient is entered/received and ending at time t3 when the guidelines/protocol indicates sufficient monitoring has been conducted. In the example shown in FIG. 4, the ideal monitoring time may be 24 hours. However, the ideal amount of monitoring time does not account for the time needed to actually connect and disconnect the patient from the monitoring device(s), nor does it account for the time it takes for a clinician to see that the recommended time of monitoring has elapsed and enter the order for the disconnect.

The second plot of the third set of plots 431 shows an order to order duration, commencing when the order is received to start patient monitoring at time t1 until the order is received to stop patient monitoring at time t4. While the order to order duration accounts for the time for the clinician to enter the disconnect order, it still does not account for the time for actually connecting and disconnecting the patient.

The third plot of the third set of plots shows the duration for an episode, which includes the entire time shown in FIG. 4, starting from when the order was received at time t1 until the patient was actually disconnected at time t5. The episode is longer than the ideal monitoring time and longer than the order to order duration, given the time taken to actually connect the patient, enter the order to disconnect, and disconnect the patient. For example, the duration of the episode may be 30 hours, which is six hours longer than the ideal time. The duration of the episode may be longer than necessary and may result in periods of missed patient monitoring during critical to care periods of time, such as right after the patient has been ordered to undergo monitoring. For example, a non-tracked alert 419 is shown along the bottom of FIG. 4, indicating a patient event (e.g., arrhythmia, low SpO2) that would have triggered an alert had the patient actually been monitored by the monitoring devices. Thus, as described above, the embodiments disclosed herein (e.g., according to the methods shown in FIGS. 6 and 7) may act to reduce the delay from when the order to monitor the patient is received to when the patient is actually connected to the monitoring device(s), reduce the delay from when the guidelines/protocols indicate the patient can be disconnected to when the order to disconnect the patient is entered, and reduce the delay from when the order to disconnect the patient is entered to when the patient is actually disconnected.

The fourth plot in the third set of plots 431 shows a monitor to discharge duration, which extends from when monitoring actually commences at time t2 and ends when the disconnect order is entered. The monitor to discharge duration may be 26 hours. The fifth plot of the third set of plots 431 shows the actual monitoring time, extending from time t2 when the patient was connected to time t5 when the patient was disconnected. In the example shown, the actual monitoring time is 27 hours.

Thus, the third set of plots 431 shows ideal or target durations for patient monitoring relative to actual patient monitoring durations, highlighting areas of delay where patient monitoring compliance may be improved. For example, as shown in FIG. 4, a first delay 414 occurs between time t1 where the order to monitor the patient is entered to time t2 where the patient is actually connected to the monitoring device(s). In the example shown, the first delay may be 3 hours. The first delay 414 may be minimized by tracking the duration of the first delay 414 and outputting an alert if the first delay 414 exceeds a first threshold duration. For example, a first alert 418 may be output once the first delay 414 reaches the first threshold duration (e.g., 30 minutes), which may act to notify and remind one or more care providers that the patient has not been connected to the monitoring device(s) yet. A second delay 416 occurs between time t4 and t5, where the order to disconnect the patient is entered at t4 and the patient is actually disconnected at time t5. The second delay 416 may be 4 hours, in the example shown. The second delay 416 may be minimized by tracking the duration of the second delay 416 and outputting an alert if the second delay 416 exceeds a second threshold duration. For example, a second alert 426 may be output once the second delay 416 reaches the second threshold duration (e.g., 30 minutes), which may act to notify and remind one or more care takers that the patient has not been disconnected from the monitoring devices yet. An additional delay may be the time between the recommended termination of monitoring (e.g., at time t3) and when the order was actually entered to disconnect the patient (e.g., at time t4), which may be 2 hours. Further, as appreciated by the plot for the I lead of the ECG, a lead failure occurred after time t4, which is after the order to disconnect the patient had been entered. The monitoring device may output an alarm when the lead failure occurs, which may be an example of an unnecessary alarm that may distract the care providers, use resources unnecessarily, etc. The alarm may be unnecessary because the ECG monitoring was not supposed to be occurring given the order to disconnect the patient.

FIG. 4 shows additional alerts that may be output by the patient monitoring compliance system. A third alert 420 may be output in response to determining that the IBP probe has been connected to the patient and is collecting IBP monitoring data. Because the patient monitoring protocol does not include IBP parameter monitoring, the inclusion of IBP monitoring is an example of the patient being over-monitored, and an alert may be output so that the patient may be disconnected from the IBP probe. A fourth alert 421 may be output in response to the signal artifacts 402 exhibited in the ECG lead signals. The monitoring device(s) and/or management system 100 may be configured to output threshold-based alarms (such the high heart rate alarm, low heart rate alarm, etc.) and may further output alarms when a lead is unattached or a monitoring device battery is low, and/or when the signal is choppy or the quality is low. Low signal quality and/or artifacts may cause the collected monitoring data to be inaccurate or unreadable, and thus the patient monitoring compliance system may determine when a monitoring device signal (e.g., sent from the monitoring device to the patient monitoring compliance system and/or an intermediary device) has a low quality and output an alert in response to the detected low quality signal. A fifth alert 422 may be output at time t3 in response to the determination that the patient has been monitored for the duration indicated by the guidelines/protocols, and a sixth alert 424 may be output at time t4 in response to the disconnect order being entered.

Thus, using the timeline in FIG. 4 as an example, various compliance metrics may be determined. For example, a relative amount of wasted time relative to the ideal amount of monitoring time may be 25% (e.g., the duration of the episode, 30 hours, minus the ideal duration, 24 hours, divided by the ideal duration of 24 hours). A relative amount of resource over utilization (e.g., unnecessary monitored time) may be 13%. The amount of excess time before connection may be 2.5 hours (e.g., with a target time to connect being 30 minutes) and the amount of excess time before disconnection may be 3.5 hours.

The monitoring effectiveness with respect to monitoring device connection may be 25% at 4 hours-post monitoring order (1 hour of monitoring over a duration of 4 hours since the order being placed) and 63% at 8 hours (5 hours of monitoring over 8 hours since the order being placed). The monitoring effectiveness with respect to the ECG may be 25% at 4 hours (with a target of 70%), 38% at 8 hours (with a target of 80%), and 63% at 24 hours (with a target of 90%). In the example shown in FIG. 4, the time in an alarm state may be 7 hours, the time in a limit alarm state may be 5 hours, and the time in a dysrhythmia alarm state may be 2 hours.

Referring now to FIG. 5, an exemplary, non-limiting block diagram is shown schematically illustrating a patient index including a list of patients and patient information assembled by the patient monitoring compliance management system of FIG. 1B. In some embodiments, the patient monitoring management compliance system 100 may execute the methods described below with reference to FIGS. 6-7 in order to generate the patient list as illustrated schematically by FIG. 5. While FIG. 5 will be described as including telemetry monitoring data from telemetry monitoring devices in order to track telemetry monitoring compliance, it is to be understood that bedside device data from bedside devices may likewise be tracked, and that the monitoring compliance may include bedside monitoring compliance as well or a combination thereof.

With respect to FIG. 5, several features shown by FIG. 1B and described above are schematically shown in order to illustrate information acquisition, aggregation, and analysis by the patient monitoring compliance management system 100. The patient monitoring compliance management system 100 receives information (e.g., data) transmitted through the network 112 from different sources, such as the telemetry monitoring devices 102, bedside devices 142, EMR database 108, and RIS 110. FIG. 5 schematically illustrates a plurality of patients 500, some of whom are coupled to the telemetry monitoring devices 102 and/or bedside devices 142 and others of whom have received orders to be coupled to the telemetry monitoring devices and/or bedside devices but have not yet been coupled to the telemetry monitoring devices and/or bedside devices, with the telemetry monitoring devices 102 configured to transmit monitoring data 502 to the patient monitoring compliance management system 100 via network 112 and the bedside devices 142 configured to transmit monitoring data 502 to the patient monitoring compliance management system 100 via the network 112. For example, Patient F is shown coupled to ECG sensor 540 and SpO2 sensor 542, with the ECG sensor 540 configured to transmit ECG monitoring data 536 to the patient monitoring compliance management system 100 and SpO2 sensor 542 configured to transmit SpO2 monitoring data 538 to the patient monitoring compliance management system 100. The ECG monitoring data 536 and SpO2 monitoring data 538 is shown schematically by FIG. 5 for illustrative purposes. Further, patient monitoring compliance management system 100 receives monitoring data 502 from each of the telemetry monitoring devices 102 and/or bedside devices 142 coupled to the patients 500. The patients 500 may be a portion of a patient population of a treatment facility (e.g., hospital), and the treatment facility may include additional patients that are not monitored via patient monitoring (e.g., patients that do not have telemetry monitoring devices 102 and/or bedside devices 142 coupled to them).

The patient monitoring compliance management system 100 additionally receives data (e.g., patient information) from the systems and databases, such as EMR database 108. FIG. 5 schematically shows patient records 504 as an array including a plurality of sub-arrays. Specifically, the patient records 504 include a list of patient names 510 (e.g., patient list) illustrated as a first sub-array, patient diagnoses/indications 512 illustrated as a second sub-array, patient monitoring orders 514 illustrated as a third sub-array, and patient alarm states 516 illustrated as a fourth sub-array. The patient records 504 are illustrated as being transmitted from EMR database 108 to patient monitoring compliance management system 100 via network 112, although the patient information may be obtained from alternative or additional systems and databases.

The patient monitoring compliance management system 100 may receive additional patient information in the form of scheduled imaging sessions 506 from RIS 110. FIG. 5 schematically shows scheduled imaging sessions 506 as an array including a plurality of sub-arrays, similar to patient records 504. The scheduled imaging sessions 506 include a list of patient names 518 illustrated as a first sub-array and a list of scheduled imaging sessions 520 illustrated as a second sub-array. The list of scheduled imaging sessions 520 includes a list of past or future imaging sessions for each patient in the patient list 518. The scheduled imaging sessions 506 are illustrated as being transmitted from RIS 110 to patient monitoring compliance system 100 via network 112. The patient monitoring compliance management system may utilize the scheduled imaging sessions to adjust for or correct an amount of unmonitored time for each patient that is currently undergoing monitoring, for example by calculating a total unmonitored time for each patient and subtracting any time spent in an imaging session from the total unmonitored time (e.g., for a given patient) to determine an amount of unplanned unmonitored time. For example, during an MRI, any telemetry monitoring devices connected to the patient to be imaged may be temporarily removed to avoid issues caused by metal in the MRI bore.

The patient monitoring compliance management system 100 generates (e.g., compiles) patient list 508 and stores the patient list 508 in memory 116, as illustrated schematically by FIG. 5. In the embodiment shown by FIG. 5, generating the patient list 508 includes compiling the patient list 508 by combining the data received by the patient monitoring compliance management system 100 from the telemetry monitoring devices 102 (e.g., telemetry monitoring data 502), bedside devices 142, CPOE system 107, EMR database 108 and/or other systems and databases (e.g., patient records 504), and RIS 110 (e.g., scheduled imaging sessions 506). By combining the data from the different sources described above, the patient list 508 may include a wide variety of patient information and may be utilized by the patient monitoring compliance management system 100 to determine whether any alerts/notifications should be output, as described below with reference to methods 600 and 700 of FIGS. 6 and 7. The patient list 508 may also be output on a suitable display device so that clinicians, administrators, or other medical facility personnel may assess patient monitoring status and compliance as well as logged or stored in a database 141 or similar for later review, reporting, analysis, etc.

The exemplary, non-limiting patient list 508 shown schematically by FIG. 5 includes a list of patient names 522, diagnoses/indications 524, ECG monitoring data 526, SpO2 monitoring data 528, time to connect and time to disconnect data 530, monitoring duration elapsed 532, percent monitored time with respect to the proper parameters used 534, time in alarm 544 (including time in a technical alarm state, time in an arrhythmia alarm state, and time in a limit alarm state), time in proximity 546 (which may indicate the amount of time a clinician or other care provider was in proximity to the patient), and percent monitoring efficiency 548 (which may include a percentage monitoring efficiency and a percentage of alarm time). In some embodiments, the patient monitoring compliance management system 100 may generate the monitoring duration elapsed 532 for each patient based on a difference between a time at which monitoring data (e.g., ECG monitoring data 526 and/or SpO2 monitoring data 528) is initially received for the patient (e.g., a time at which monitoring data is first received) and a time at which the patient list 508 is generated (e.g., compiled by the patient monitoring compliance system 100). In other embodiments, the patient monitoring compliance management system 100 may continuously track (e.g., measure) a current time and may compare the tracked time to the time at which monitoring data is first received for each patient in order to determine the monitoring duration elapsed 532 for each patient. The monitoring duration elapsed corresponds to a monitoring duration for each patient (e.g., an amount of time each patient has been monitored via telemetry monitoring and/or bedside devices). In still further examples, the monitoring duration that has elapsed may include the time at which an order was placed to being monitoring to the current time. Once a patient has been disconnected from the monitoring device(s) per a disconnect order, that patient may be removed from the patient list.

The lists of patient names (e.g., 510, 518, and 522) may each be the same in some embodiments and may be utilized by the patient monitoring compliance management system 100 in order to link patient information (e.g., diagnosis from diagnoses 512, scheduled imaging sessions from 520, monitoring data from telemetry monitoring devices 102, etc.) from the different data sources with the corresponding patient in the patient list 508.

The patient list 508 may be output by the compliance module 118 of the patient monitoring compliance management system 100. The compliance module 118 may interface with processors 120 and/or analyzer module 208 in order to generate the patient list 508 and output the patient list 508 for display. In some embodiments, the monitoring status of each patient may be determined by the patient monitoring compliance management system 100 based on the patient monitoring data (e.g., ECG monitoring data 526 and/or SpO2 monitoring data 528), monitoring orders 530, and/or monitoring duration elapsed 532 and may be stored in the memory 116 of the patient monitoring compliance management system 100. In some embodiments, in addition to the duration of monitoring ordered, the monitoring orders 530 may include orders by the care providers to initiate monitoring of a patient or to cease monitoring of a patient. The monitoring status of each patient may include an indication of whether the patient is currently monitored via telemetry and/or bedside monitoring (e.g., as determined by whether monitoring data is currently received for the patient by the patient monitoring compliance management system), and the monitoring status may further include an indication of whether an order to initiate monitoring or cease monitoring has been made for the patient. The patient monitoring status may each be stored in the memory 116 of the patient monitoring compliance system 100. The on-going collected, aggregated, and analyzed data and associated patient information, statuses, etc., besides being displayed on output devices, may be logged or stored in a database 141 or similar for later review, reporting, analysis, etc.

In some embodiments, a graphical user interface (GUI) displayed at a display device of the patient monitoring compliance management system, such as the display device 126 shown by FIG. 1 and described above, may be configured to display a patient list (such as the patient list described above) output to the display device by a compliance module of the patient monitoring compliance system, such as compliance module 118 shown by FIG. 1B and described above. Further, rather than show all the patients for a given medical facility, a patient list may be generated for a given unit of a medical facility, a given department of a medical facility, a group of caregivers, etc.

Turning now to FIG. 6, a flow chart of a method 600 for managing a patient monitoring protocol via a patient monitoring compliance management system is shown, according to an exemplary embodiment. Method 600 may be implemented by the patient monitoring compliance management system 100 shown in FIG. 1B. In some embodiments, method 600 may be implemented as executable instructions in a compliance module of a patient monitoring compliance management system, such as the compliance module 118 of FIG. 1B. The conditional states, output, alerts generated, etc. by the method 600, besides being displayed on output devices, may be logged or stored in a database 141 or similar for later review, reporting, analysis, etc.

At 602, an order is received for parameter monitoring of a patient. The order may be received by the compliance module from a CPOE system, such as CPOE system 107 of FIG. 1B, or another suitable source (such as a clinician directly entering the patient monitoring order to the patient monitoring compliance system). The order may specify the patient that is to be monitored, the provider submitting the order, the current condition of the patient, the patient's diagnosis, and treatment instructions to be administered such as monitoring via a patient monitor. At 604, a monitoring protocol for the patient is determined. For example, the patient monitoring compliance management system may obtain protocol and/or indication information to be followed during care of the patient at the medical facility. As explained above, the protocol information may include protocols or standards for patient parameter monitoring for a plurality of different indications or patient conditions. The protocol and/or indication information may include current patient indication or condition (e.g., as diagnosed by a care provider and entered into the CPOE system and/or EMR) and the patient monitoring protocol(s) for that indication or condition. The patient monitoring protocols may include a recommendation for which patient parameters are to be monitored (e.g., ECG, CO2, blood pressure, heart rate, temperature, blood oxygen level, etc.) and a recommended monitoring duration for each recommended monitoring parameter, such as monitoring blood pressure every four hours for 24 hours, monitoring with a 6-lead ECG for 24 hours, and monitoring SpO2 for the first 12 hours. The patient monitoring protocol may be a standard protocol selected from a protocol library (e.g., on protocols/standards system 111) based on the diagnosis or may be a department-based protocol or physician-ordered protocol.

At 606, method 600 determines if the monitoring environment is ready to monitor the patient according to the selected monitoring protocol. For example, once the patient monitoring order is received, a check may be performed to determine monitoring readiness. The check may include determining, for each recommended monitoring parameter, if a device configured to monitor that parameter is available/in proximity to the patient (e.g., in the patient room), if the device is configured with the correct parameter support/modules per the diagnosis/protocol, etc. If the monitoring environment is not ready to monitor the patient per the protocol, method 600 proceeds to 608 to output an alert notifying one or more users that the monitoring environment is not ready to monitor the patient. The alert may be a visual and/or audio alert, and may be output on a suitable display device, such as display device 126. In some examples, the alert may be pushed to one or more display devices operatively coupled to the patient monitoring compliance system, such as via alert notification system 132. In this way, one or more clinicians caring for the patient may be notified of the lack of monitoring readiness, via display devices associated with the clinicians. In some examples, the alert may persist and/or be intermittently output until a user acknowledges, dismisses, or silences the alert and/or until the patient monitoring environment is ready to monitor the patient. Upon outputting the alert, method 600 loops back to 606 to continue to assess if the environment is ready to monitor the patient.

If the monitoring environment is ready to monitor the patient, method 600 proceeds to 610 to identify/track the status of data flow/collection of the monitoring device(s) for the patient by parameter/parameter set. Determining the status of data flow/collection of the monitoring device(s) for the patient may include identifying which patient parameters are to be monitored (e.g., from the order received at 602 and/or the from the protocol determined at 604) and determining whether patient monitoring data monitoring the indicated patient parameters is transmitted from one or more monitoring devices to the patient monitoring compliance system for the patient. In one embodiment, the monitoring devices may be the telemetry monitoring devices 102 and/or the bedside devices 142 shown by FIG. 1B and described above. The monitoring devices may transmit data such as patient heart rate, patient peripheral capillary oxygen saturation, patient events (e.g., irregular heart rhythms), patient respiration rate, patient blood pressure, patient heart rhythm, patient temperature, etc., to the patient monitoring compliance system for each patient coupled to the monitoring devices. As one example, each patient undergoing monitoring may be coupled to one or more monitoring devices with varying sensors (e.g., an ECG sensor, SpO2 sensor, NIBP sensor, respiration sensor, temperature sensor, etc.), and the patient monitoring compliance management system may acquire monitoring data from each of the monitoring devices. The status of the data flow/collection of the monitoring devices may include whether data is being transmitted/received, whether the data indicates an alarm condition (per each parameter being monitored), whether the data indicates any limit violations, whether the data indicates the patient is off network/no telemetry (when data is not received for a given parameter), whether a probe is disconnected, etc.

At 612, method 200 determines if the patient is connected to the one or more monitoring devices dictated by the monitoring order and/or selected monitoring protocol. The determination of whether the patient is connected to the one or more monitoring devices may be based on whether the patient monitoring compliance management system has received any data from the identified monitoring devices for the patient. Once a patient is connected to a monitoring device and that monitoring device collects patient monitoring data, the patient monitoring data may be streamed to the patient monitoring compliance management system. In some patient monitoring devices, an intermediate step of admitting the patient to the device may occur but the patient may not be connected to the device and transmitting data. This intermediate step may be captured, analyzed, and reported on by the patient monitoring compliance management system 100 in some embodiments.

If the patient is not connected to the one or more monitoring devices, method 600 proceeds to 614 determine if a threshold amount of time has elapsed since the order to monitor the patient was entered. The threshold amount of time may be 30 minutes in one example. In some examples, the threshold amount of time may be set by a user, such as an administrator of the medical facility or by a clinician overseeing the patient. If the threshold amount of time has not elapsed, method 600 proceeds back to 610 to continue to track the status of the data flow/collection of the monitoring device(s). If the threshold amount of time has elapsed, method 600 proceeds to 616 to output an alert notifying one or more users of the delay in connecting the patient to the one or more monitoring devices. The alert may be a visual and/or audio alert, and may be output on a suitable display device, such as display device 126. In some examples, the alert may be pushed to one or more display devices operatively coupled to the patient monitoring compliance system, such as via alert notification system 132. In this way, one or more clinicians caring for the patient may be notified of the delay, via display devices associated with the clinicians. In some examples, the alert may persist and/or be intermittently output until a user acknowledges, dismisses, or silences the alert and/or until the patient is connected to the one or more monitoring devices. Upon outputting the alert, method 600 loops back to 610 to continue to track the status of the data flow/collection of the monitoring devices. It should be understood that in some examples, different telemetry and/or bedside monitoring devices may be connected to the patient at different times and/or probes/leads of the different monitoring devices may be connected to the patient at different times. Thus, the decision of whether the patient is connected to the one or more monitoring devices may be made on a device by device or parameter by parameter basis, such that an alert may be output if a first monitoring device (or sensor probe/lead) is not connected to the patient within the threshold amount of time, even if a second monitoring device (or sensor probe/lead) is connected to the patient within the threshold amount of time. In some examples, the various monitoring parameters may be ranked (e.g., based on the monitoring protocol) and only relatively high ranking parameters may be monitored for connection compliance. For example, a first protocol may indicate that all ordered parameters are relatively high ranking, such that if any of the ordered parameters are not monitored within the threshold time, an alert is output. However, a second protocol may indicate that a first monitoring sensor/parameter (e.g., pulse oximeter) is high ranking while a second monitoring sensor/parameter (e.g., temperature sensor) is low ranking, and an alert may be output if the first monitoring sensor/parameter is not connected to the patient within the threshold time but an alert may not be output if the second monitoring sensor/parameter is not connected to the patient within the threshold time. Further still, in some examples, different monitoring parameters may have different threshold times associated with them. In the example presented previously, an alert may be output if the second monitoring sensor is not connected to the patient after a second, longer threshold amount of time has elapsed.

Returning to 612, if it is determined that the patient is connected to the one or more monitoring devices, method 600 proceeds to 618 to performing ongoing tracking of monitoring compliance, which will be explained in more detail below with respect to FIG. 7. Briefly, during ongoing monitoring of patient compliance, data from the one or more monitoring devices is analyzed by the patient monitoring compliance system in order to determine, over a duration, a relative amount of time that the data from the one or more medical devices was usable for monitoring one or more parameters of the patient. The relative amount of time may be determined by tracking unmonitored time (e.g., due to sensor/lead removal, device/battery failure, patient leaving a monitoring range such that monitoring data is not received, or other signal quality issues, such as signal artifacts), and the tracked unmonitored time may be corrected by planned unmonitored time (e.g., diagnostic imaging sessions, personal hygiene events) and/or a location of one or more clinicians relative to the patient (which may count as monitored time if the one or more clinicians are interacting/caring for the patient). For example, an amount of unmonitored time over a 10 hour duration may be determined by analyzing the signal quality of the data from the monitoring device(s) over the 10 hour duration to determine a total duration (e.g., a total number of minutes) where the data from the one or more monitoring devices was not usable to monitor the indicated parameters of the patient (whether due to low signal quality or missing data due to lead failure or signal transmission or reception failure). The total duration where the data was not usable may be adjusted based on the planned unmonitored time and/or location of the one or more clinicians to arrive at a total amount of monitored time, which may be normalized based on a total duration of presumed monitoring time (e.g., from when the patient was connected to the monitoring devices to the current time) to arrive at the relative amount of monitored time. If the relative amount of monitored time is less than a threshold, a notification may be output alerting one or more users (e.g., administrators, clinicians) that the monitoring of the patient is not in compliance due to the relatively long duration of the unmonitored time. Further, the ongoing tracking of monitoring compliance may include tracking an alarm state duration when any of the monitoring devices connected to the patient are in an alarm state and outputting a notification when the alarm state duration is greater than a threshold. The notifications that may be output by the patient monitoring compliance management system during the ongoing tracking of monitoring compliance may be in addition to any alarms generated by the individual monitoring devices.

Returning to FIG. 6, at 620, method 600 determines if a disconnect order has been received. The disconnect order may indicate that a clinician has ordered the patient be disconnected from the monitoring device(s). The disconnect order may be received by the compliance module from a CPOE system, such as CPOE system 107 of FIG. 1B, or another suitable source (such as a clinician directly entering the patient monitoring order to the patient monitoring compliance system). If a disconnect order has not been received, method 600 loops back to 618 to continue to perform the ongoing tracking of monitoring compliance. If a disconnect order has been received, method 600 proceeds to 622 to track the status of the data flow/collection of the monitoring device(s), specifically to determine if the data flow from the monitoring devices has stopped (indicating the patient has been disconnected) or if a patient discharge action has been detected or received by the monitoring device after the patient has been discharged from the monitor by a caregiver. At 624, method 600 determines if the patient has been disconnected from the monitoring devices, which may be based on the data flow/collection tracking performed at 622 and/or based on another mechanism (e.g., a clinician entering an input indicating the patient has been disconnected). If the patient has not been disconnected, method 600 proceeds to 626 to determine if a threshold amount of time since the disconnect order was entered has elapsed. The threshold amount of time may be 30 minutes or another suitable amount of time and may be set by a user. If the threshold amount of time has not elapsed, method 600 loops back to 622 to continue to track the status of the data flow/collection of the monitoring device(s). After the disconnect order is received and before the patient is actually disconnected from the monitoring device(s), the ongoing tracking of the monitoring compliance may continue to be performed, at least in some examples.

If the threshold amount of time has elapsed, method 600 proceeds to 628 to output an alert to notify one or more users of the delay in disconnecting the patient from the monitoring device(s). The alert may be a visual and/or audio alert, and may be output on a suitable display device, such as display device 126. In some examples, the alert may be pushed to one or more display devices operatively coupled to the patient monitoring compliance system, such as via alert notification system 132. In this way, one or more clinicians caring for the patient may be notified of the delay, via display devices associated with the clinicians. In some examples, the alert may persist and/or be intermittently output until a user acknowledges, dismisses, or silences the alert and/or until the patient is disconnected from the one or more monitoring devices. Upon outputting the alert, method 600 loops back to 622 to continue to track the status of the data flow/collection of the monitoring devices. It should be understood that in some examples, different monitoring devices or monitoring sensors may be disconnected from the patient at different times, and the decision of whether the patient is disconnected from the one or more monitoring devices/sensors may be made on a device by device (or parameter by parameter) basis, similar to the approach explained above for the determination of whether the patient has been connected to the monitoring devices.

Returning to 624, if it is determined that the patient has been disconnected from the monitoring devices, method 600 proceeds to 630 to determine final analytics for the patient and display the analytics in a patient list and/or archive the final analytics. Before reviewing 630, it is understood while methods 600 and 700 process (described below), analytics, reporting, etc. continue to occur and update patient list 508 and the like. The final analytics may include the amount of time from when the monitoring order was received until the patient was actually connected (time to connect) and the amount of time from the when the monitoring disconnect order was received until the patient was actually disconnected (time to disconnect). The analytics may further include monitoring compliance results determined during the ongoing tracking of monitoring compliance, such as unmonitored time (whether for each monitoring device individually or multiple monitoring devices collectively), time in alarm states, and other compliance metrics. The patient list may include but is not limited to a list of patients at the medical facility who are undergoing or underwent monitoring (e.g., over a given duration, such as the past day, week, month, etc.) summarized at the department, unit, facility, system, and/or care provider level, and the patient list may include, for each patient in the list, a time to connect, time to disconnect, unmonitored time, time in alarm states, and/or other compliance metrics. An example of a patient list is shown in FIG. 5 and explained above.

FIG. 7 is a flow chart illustrating a method 700 for ongoing tracking of monitoring compliance. Method 700 may be implemented by the patient monitoring compliance management system 100 shown in FIG. 1B. In some embodiments, method 700 may be implemented as executable instructions in a compliance module of a patient monitoring compliance management system, such as the compliance module 118 of FIG. 1B. In some embodiments, method 700 may be implemented as part of method 600, for example in response to determining that the patient has been connected to the one or more monitoring devices. The conditional states, output, alerts generated, etc. by the method 700 besides being displayed on output devices may be logged or stored in a database 141 or similar for later review, reporting, analysis, etc.

At 702, data flow parameters and system and alarm status is determined by parameter, parameter set, or device for each monitoring device and parameters with/for which the patient is ordered to be monitored. The data flow parameters may include, for each monitoring device sensor, whether data is being sent from the monitoring device sensor and received by the appropriate receiver (e.g., EMR, medical facility/clinician computing device, patient monitoring compliance system data aggregation/analyzer or database), the signal quality of the data sent by the monitoring device sensor, and/or any other data flow parameters that may indicate whether the data is usable to monitor the patient. The alarm status may include, for each monitoring device, if that monitoring device is currently in an alarm state, the category of alarm (e.g., technical, limit, arrythmia), the type or name of the alarm (e.g., leads fail, SpO2, ventricular tachycardia), the alarm's duration, etc. The monitoring device may enter into an alarm state when a value of a patient parameter monitored by the monitoring device/sensor (e.g., an SpO2 value as measured by a pulse oximeter) reaches a predetermined condition, such as a predetermined condition relative to a threshold (e.g., the SpO2 value drops below a threshold value) and/or a predetermined condition that indicates probe/device issues, such as a probe (e.g., SpO2 probe) becoming disconnected, poor signal quality, etc. The monitoring device may also enter an alarm state when the analysis of the parameter information (e.g., waveform morphology) indicates a dysrhythmia event or condition has been identified (e.g., asystole, pause, atrial fibrillation) has occurred. The monitoring device may remain in the alarm state until the patient parameter no longer meets the predetermined condition and/or until a user (e.g., a clinician attending to the patient) silences or dismisses the alarm.

At 704, method 700 determines if the patient is currently over- or under-monitored. As explained above with respect to FIG. 6, the parameters of the patient that are being monitored may be indicated by a monitoring protocol. The patient monitoring compliance management system may compare the parameters currently being monitored (e.g., based on whether data is being received from monitoring device(s)/sensors configured to monitor those parameters) to the monitoring protocol to determine if the monitoring protocol is being met, or if the patient is being over- or under-monitored. The patient may be over-monitored when one or more patient parameters (e.g., blood pressure, CO2, SpO2, etc.) are being monitored that are not indicated by the monitoring protocol. The patient may be under-monitored when one or more patient parameters indicated by the monitoring protocol are not currently being monitored. If the patient is currently over- or under-monitored, method 700 proceeds to 706 to output an alert notifying one or more users/care providers that the patient is over- or under-monitored. The alert may be output on a display device, similar to the output of the alerts described above with respect to FIG. 6. Upon outputting the alert, method 700 loops back to 702 to continue to determine data flow parameters and alarm status for each parameter/monitoring device.

If the patient is not currently over- or under-monitored, method 700 proceeds to 708 to optionally track a location of one or more members of the care team assigned to care for the patient and/or track planned unmonitored time for the patient. It is envisioned the patient's location may also be tracked. In one embodiment, the location of the caregiver may be used to adjust the unmonitored time for when the caregiver is in the patient's room. Additionally, a care team member's proximity to the patient may be captured and used to adjust aspects of the monitoring time. For instance, if the patient is ambulating outside of their room with the assistance of a care team member, the proximity of the caregiver could be included to adjust the monitoring time. The planned unmonitored time may include time spent in diagnostic imaging sessions (e.g., performed with a suitable imaging system, such as a magnetic resonance imaging (MRI) system, a computed tomography (CT) imaging system, or other imaging system where presence of the monitoring devices/leads of the monitoring devices may disrupt imaging), time spent in patient hygiene events (such as baths or showers), and/or any other time spent where the patient is purposely not monitored with the monitoring devices. As explained above with respect to FIGS. 1A and 1B, the location of the one or more members of the care team assigned to care for the patient may be tracked using RTLS or another suitable tracking system. If a member of the care team is within a certain distance of the patient (e.g., within 1-3 meters), the member may be considered to be monitoring/attending to the patient.

At 710, a relative amount of monitored time and a time in alarm state are determined based on the data flow parameters, alarm status, care team location, and/or planned unmonitored time. The time in alarm state may be determined as a total amount of time that any of the monitoring parameters/devices connected to the patient was issuing an alarm, and/or the time in alarm state may be determined as a current respective amount of time that each monitoring parameter/device is issuing an alarm. The active and cumulative time in an alarm state also may be determined at the alarm category level and/or by the specific alarm type for use in identifying non-compliant extended alarm state conditions. For example, if a patient oxygen saturation drops below a threshold, the SpO2 monitoring component may issue a local/device alarm, an alarm to a patient monitoring central station, and an alarm to the patient monitoring compliance system. The time in alarm state may track how long the SpO2 device issues the alarm (e.g., before the alarm is silenced by a user), while also adding the current alarm time to the totaled cumulative time in alarm for a given parameter, in this case SpO2. The time in alarm state may track the time in alarm for each monitoring parameter, and may aggregate the time in alarm for all monitoring parameters. Thus, at 710, the state conditions for each monitored parameter are determined along with composite or groupings at a parameter set level (e.g., ECG— lead I, II, II, Va) and at a patient-level. The time in these alarm-related conditions may be used to determine a time in alarm relative to the total monitoring time (i.e., alarm burden factor) giving an indication of the degree of issues the monitoring of the patient is occurring. Such an alarm burden indicator may be used to rank the monitored patient population for need of monitoring follow-up and review. A threshold level and caregiver alerting may be used with the alarm burden indicator for proactive problem resolution by the care team.

The relative amount of monitored time may be determined based on the total duration that has elapsed since the patient was connected to the monitoring device(s) and an amount of time during the total duration that the data output by the monitoring device(s) was unusable for patient monitoring, which may each be determined from the data flow parameters. The data output by the monitoring device(s) may be deemed unusable for patient monitoring if data is not output or received (e.g., due to lead/probe failure, battery failure, etc.) or if the data is low quality or includes signal artifacts. In some examples, the amount of time that the data from the monitoring device(s) was not usable for patient monitoring may be adjusted by the planned unmonitored time and/or based on the care team location. For example, if the patient was scheduled for an x-ray imaging session, the duration of the x-ray imaging session may be subtracted from the amount of time that the data was not usable for patient monitoring. Further, if the care team is determined to have been located in the same room as the patient during a period overlapping with a period where the data was not usable for patient monitoring, that period where the data was not usable for patient monitoring may be omitted from the amount of time the data was not usable for patient monitoring, on the assumption that the care team was able to actively monitor the patient. In this way, only time where the patient was intended to be monitored but was not monitored may be tracked. In examples where the amount of unmonitored time is adjusted for planned unmonitored time and/or care team location, both metrics may be tracked and reported. For example, both a total amount of unmonitored time and a corrected amount of unmonitored time (corrected to account for planned unmonitored time and/or care team location) may be tracked and reported to users in the form of the patient list or other analytic.

The amount of time that the data from the one or more monitoring devices was not usable for patient monitoring (and in some examples corrected for planned unmonitored time and/or care team location) may be normalized based on the total duration of monitoring, e.g., as a percentage of the total duration of monitoring to arrive at the relative amount of monitored time. In some examples, the relative amount of monitored time may be determined as a rolling percentage, such as by being calculated over an hour duration of patient monitoring, a six-hour duration of patient monitoring, etc. By calculating a rolling percentage, continued notification of a period of unplanned unmonitored time that has already been tracked and of which users have already been notified may be reduced or avoided.

At 712, the relative amount of monitored time (uncorrected and/or corrected) and time in alarm state are output for display in a patient list. As explained previously, the patient list may include all patients in a given unit of a medical facility (e.g., ward, floor, unit, department, building, or the entire medical facility) or all patients being attended to by a given physician or other care provider that are undergoing monitoring (e.g., where an order has been received to monitor the patient). The patient list may include, for each patient, identifying information (e.g., name, room number), current indications or diagnoses, total duration of monitoring time, etc. The patient list may be updated in an ongoing basis to include the relative amount of monitored time, time in alarm state, partially monitored time, time within standards/compliance, time in over-monitored state, and/or time in under-monitored state for each patient, as the times are calculated.

At 714, method 700 determines if the monitoring order for the patient has been updated or changed. For example, as patient condition changes, the protocol used to monitor the patient may no longer apply, and thus a care provider attending to the patient may update, cancel, or otherwise change the monitoring order (e.g., via the CPOE system). If a change to the monitoring order is received, method 700 proceeds to 716 to output a notification of the change in the order. The notification may be output to one or more display devices (e.g., display 126 and/or other networked devices via the notification system). After outputting the notification, method 700 may return to 702 to continue to determine data flow parameters and alarm status for each parameter/monitoring device. Compliance with the changed order may then be determined at 704 where method 700 determines if the patient is over- or under-monitored.

If the order has not been changed, method 700 proceeds to 718 to determine if any of the exemplary alert thresholds have been met. The alert threshold may include a first threshold for the relative amount of monitored time, a second threshold for the time in alarm state, and/or a third threshold for the relative monitoring alarm burden time. If the relative amount of monitored time is below the first threshold, an alert threshold is met. If the time in alarm state exceeds the second threshold, an alert threshold is met. If the relative amount of monitoring alarm burden time exceeds a third threshold, an alert threshold is met. The first threshold may be 90%, as one non-limiting example. The second threshold may be five minutes, as a non-limiting example. The third threshold may be 25%, as one non-limiting example.

If an alert threshold has been met, method 700 proceeds to 720 to output an alert indicative of the alert threshold that has been met. For example, if the relative amount of monitored time is below the first threshold, an alert may be output to one or more suitable devices (e.g., display devices) to notify one or more users that the amount of monitored time for the patient is less than the threshold. The alert may be a visual and/or audio alert, and may be output on a suitable display device, such as display device 126. The alert may also be displayed and annunciated on the acquisition device 102 and 142 and other associated devices such as a central station 140. In some examples, the alert may be pushed to one or more display devices operatively coupled to the patient monitoring compliance management system, such as via alert notification system 132. In this way, one or more clinicians caring for the patient may be notified of the amount of monitored time and/or time in alarm state, via display devices associated with the clinicians. In some examples, the alert may persist and/or be intermittently output until a user acknowledges, dismisses, or silences the alert. Upon outputting the alert, method 700 loops back to 702 to continue to track unmonitored time and time in alarm state.

If an alert threshold is not met, method 700 proceeds to 722 to determine if the total duration of monitored time for each monitored parameter meets the specified monitoring duration set forth by the monitoring protocol for the patient being monitored. For example, when the patient is ordered to undergo monitoring, guidelines/protocols may be referenced to determine which parameters are to be monitored for the patient, which monitoring device(s) should be used to monitor the patient, how long the patient should be monitored for, what threshold-based alarms should be instituted, etc. The guidelines/protocols may be retrieved from the protocols/standards system 111, for example, and may be specific to (e.g., generated by) the medical facility and/or determined by a larger governing body. In some examples, the guidelines/protocols may be generated by a clinician attending to the patient or the guidelines/protocols may be generated by the medical facility and/or a governing body and modified by the clinician.

The total monitoring time for a parameter that is compared to the protocol-specified duration may be the overall monitored time for that parameter (e.g., the overall time from when that parameter was first monitored until that parameter was no longer monitored due to a disconnect order), the calculated monitored time for that parameter (where periods of lead failure, signal artifacts, etc., are subtracted from the monitored time), or both. If the total monitoring time for a given parameter (e.g., blood pressure) has not met any guideline-based duration for monitoring, method 700 loops back to 702 to continue to track monitored time and time in alarm state. If the total monitoring time for a given parameter has met a guideline-based duration for monitoring, method 700 proceeds to 724 to output a recommendation to disconnect the patient from the monitoring device (or a specific sensor monitoring a specific parameter) monitoring that parameter, for display in the patient list or other suitable location. In this way, care givers may be notified that it may be desirable to evaluate the patient for a disconnect order, in order to prevent over-utilization of monitoring resources. At 726, the patient continues to be monitored for monitored time and time in alarm state until the patient is disconnected, and then method 700 ends. It is to be understood that for each monitored parameter, a recommendation to disconnect the patient/cease monitoring of that parameter may be output when that parameter has been monitored for the specified duration, but that other parameters may still be monitored.

FIG. 8 shows an example display device 800 on which a patient monitoring alert may be displayed. In the example shown, display device 800 may be a clinician device, such as a smart phone or tablet, but the patient monitoring alert may be displayed on other types of display devices, such as laptops, desktop monitors, etc. The display device 800 may be one of the clinician/facility devices 133 of FIG. 1B.

Display device 800 includes a screen 802 on which a graphical user interface (GUI) 804 is displayed. GUI 804 presents patient monitoring data for a specified patient, herein patient A. The patient monitoring data displayed in GUI 804 includes heart rate, blood oxygen saturation, blood pressure, and temperature, but other parameters are possible. Each displayed parameter may be the most-recently obtained value for that parameter; because blood pressure and temperature are episodic/non-continuous, the time at which that parameter was obtained in also displayed.

GUI 804 further includes an alert 806. The alert 806 may be displayed at any suitable display location and may have a suitable visual appearance. The alert 806 may be generated by the patient monitoring compliance system as explained above and includes information pertaining to the patient as determined by the patient monitoring compliance management system. In the example shown, the alert is notifying the user of the display device (e.g., a clinician attending to the patient) that disconnection of the patient from a monitoring device is overdue (e.g., relative to when a disconnect order was received). By displaying alerts generated by the patient monitoring compliance system on one or more display devices (e.g., associated with one or more members of the care team attending to the patient), the care team members may be promptly notified of any monitoring delays, monitoring alarms, or unmonitored periods.

Figure 9A:
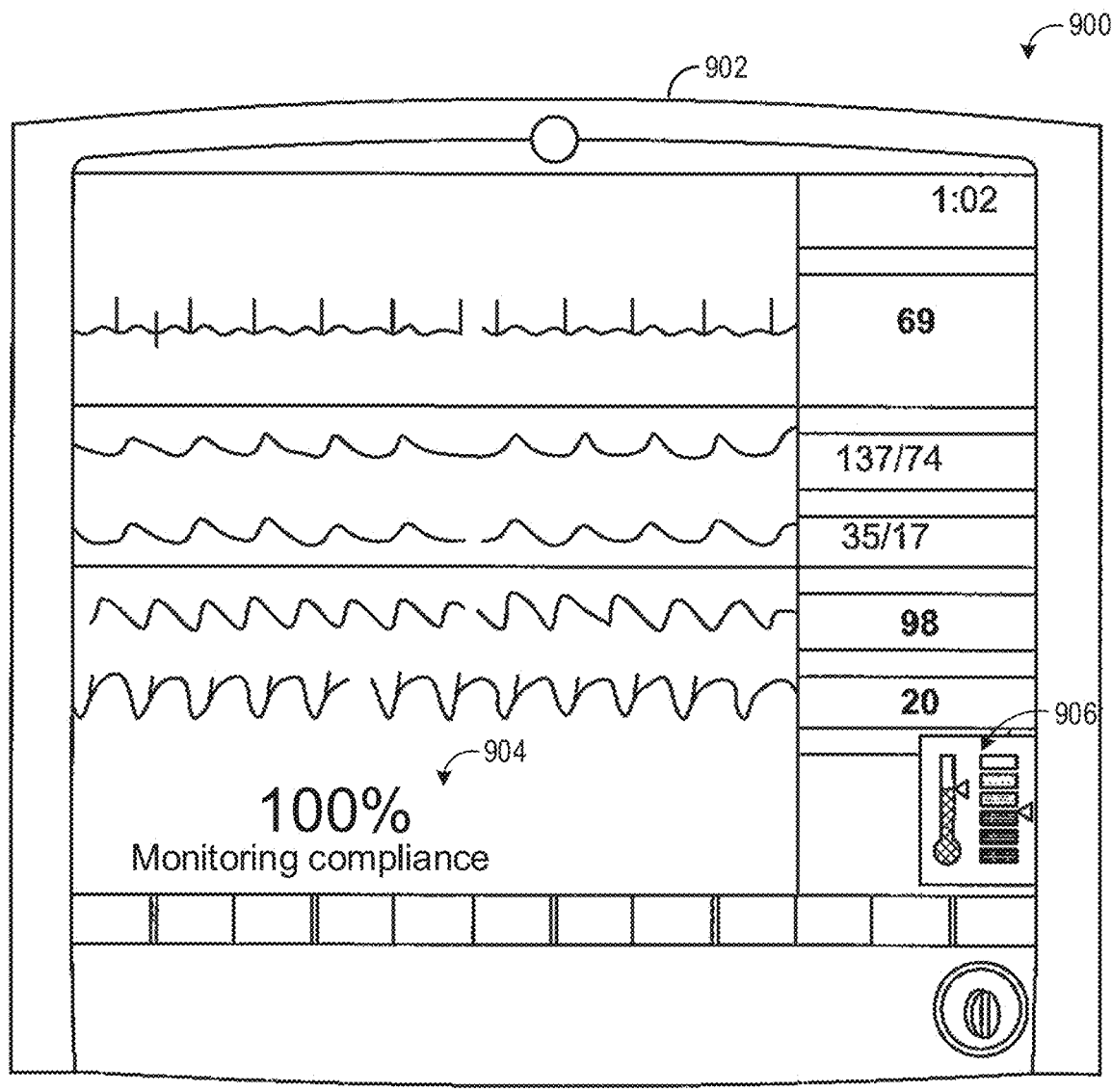
FIG. 9A shows an example GUI displayed on a display device, the GUI including a representation of a monitoring compliance metric for a patient, according to an exemplary embodiment.
Figure 10:
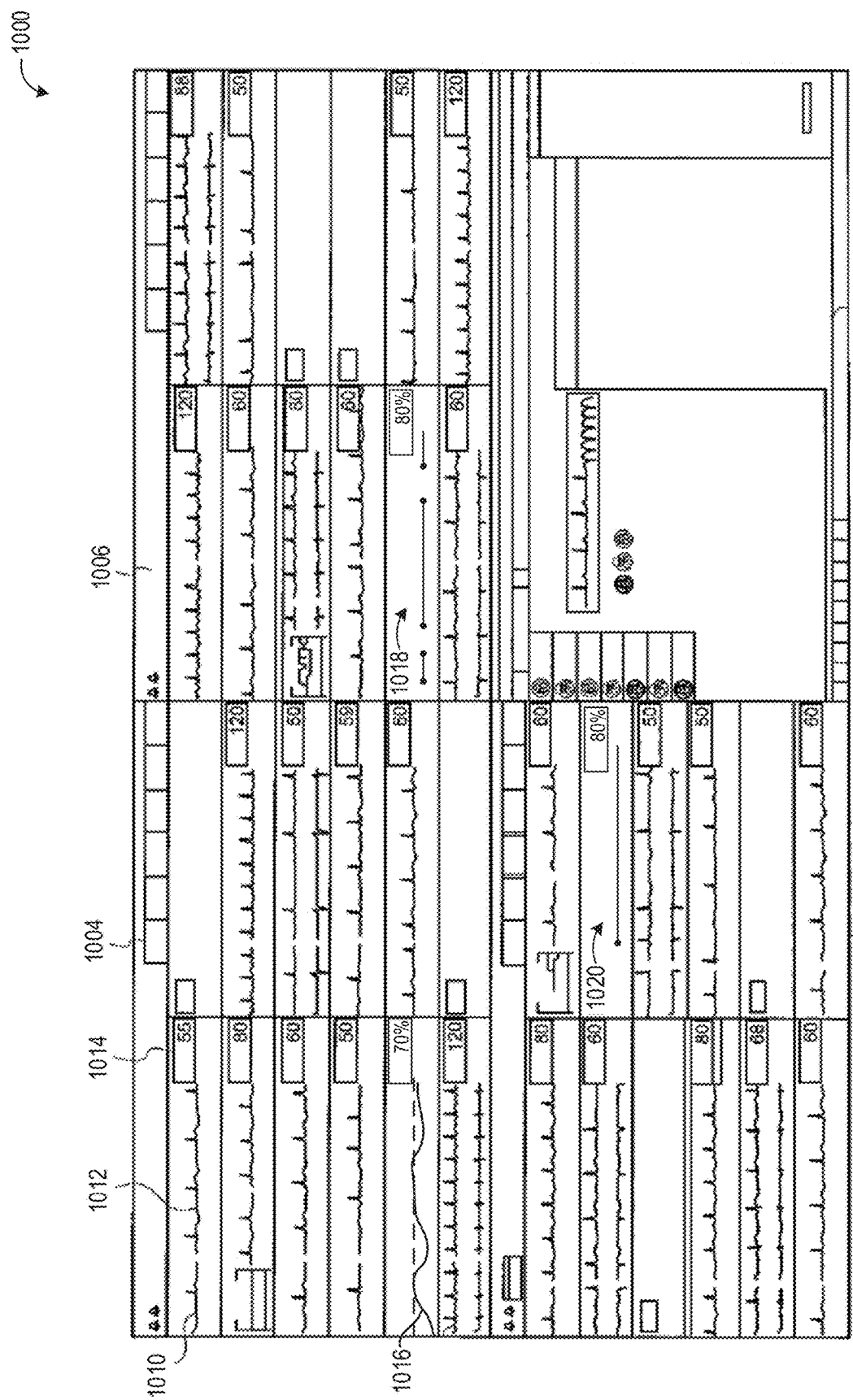
FIG. 10 shows an example GUI displayed on a display device, the GUI including a representation of monitoring compliance metrics for multiple patients, according to an exemplary embodiment.

FIG. 9A shows an example display device 902 on which a patient monitoring GUI 900 may be displayed. In the example shown, display device 902 may be associated with a bedside monitoring device, such as one of the bedside devices 142 of FIG. 1B.

GUI 900 presents patient monitoring data for a specified patient, such as heart rate, blood oxygen saturation, blood pressure, and temperature, but other parameters are possible. GUI 900 further includes a patient monitoring compliance metric 904 determined as explained above with respect to FIGS. 4 and 7. In the example shown in FIG. 9A, the patient monitoring compliance metric 904 may include an average monitoring compliance for all monitored parameters over a duration (e.g., where the duration started upon receipt of the monitoring order or where the duration started upon connection of the patient to the monitoring devices). In another example, the patient monitoring compliance metric 904 may include an averaging monitoring compliance for a specific monitored parameter, or for each monitored parameter, over the duration. In this way, a care provider may quickly assess the current monitoring compliance for the patient, which may aid the care provider in decision making regarding current and future monitoring (e.g., whether or not the monitoring time should be extended due to low compliance). It is also envisioned, other determined monitoring metrics may be displayed such as the relative alarm burden time. Additionally, a parameter compliance indicator may show if the compliant parameters are being monitored and if not the case which parameters should be added or removed. For example, two visual indicators 906 are shown in FIG. 9A. The visual indicator on the left (e.g., resembling a thermometer) may indicate an overall monitoring compliance (e.g., for all monitored parameters) while the visual indicator on the right may illustrate monitoring compliance for a single parameter, such as SpO2.

Figure 9B:
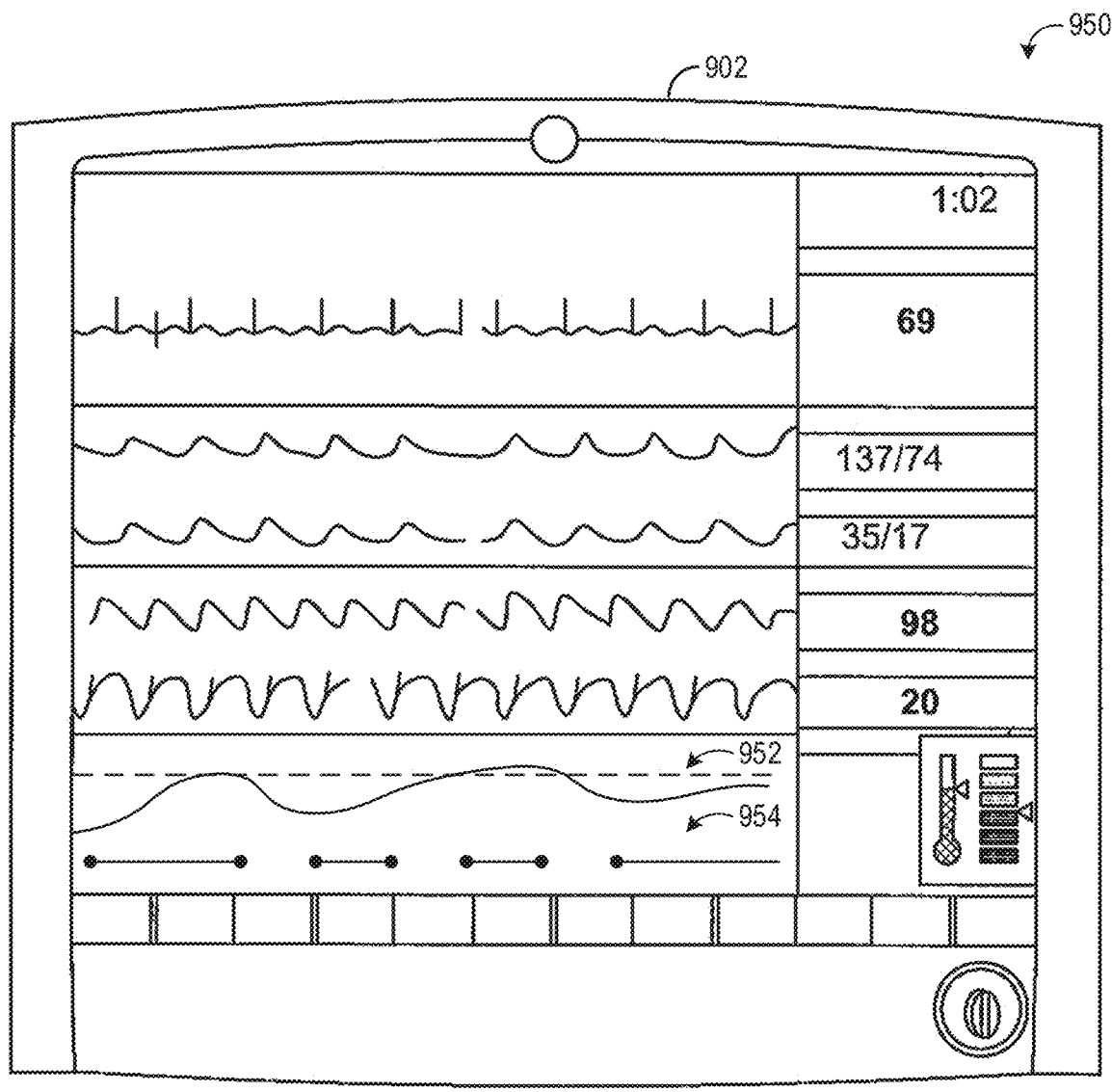
FIG. 9B shows an example GUI displayed on a display device, the GUI including a representation of a monitoring compliance metric over time for a patient, according to an exemplary embodiment.

FIG. 9B shows the display device 902 displaying a patient monitoring GUI 950. GUI 950 may be similar to GUI 900, and thus may include the same patient monitoring data for the patient (e.g., heart rate, blood pressure, etc.). In one exemplary case, GUI 950 may include two patient monitoring compliance metrics plotted over time, rather than a single value, determined as explained above with respect to FIGS. 4 and 7. The patient monitoring compliance metrics include a plot 952 of an average monitoring compliance over time relative to a target monitoring compliance, and timeline 954 of monitoring status over time, with each gap in the timeline representing periods where the patient monitoring data was not usable to monitor the patient (e.g., signal artifacts, parameter disconnected, planned unmonitored time, etc.). The plot 952 and/or the timeline 954 may be representative of all monitored parameters collectively, or the plot 952 and/or timeline 954 may be representative of a single monitored parameter. In this way, a care provider may quickly assess the monitoring compliance for the patient over time, which may aid the care provider in decision making regarding current and future monitoring (e.g., whether or not the monitoring time should be extended due to low compliance).

FIG. 10 shows an example GUI 1000 that may be displayed across one or more display devices/monitors. GUI 1000 may be displayed on a display device(s) of a central station, such as central station 140 of FIG. 1B. GUI 1000 may include patient data for a plurality of patients. For example, a first display area 1004 may display patient data for a first patient, a second display area 1006 may display patient data for a second patient, and a third display area 1008 may display data for a third patient. The displayed patient data for each patient may include waveforms and/or current values of different monitoring parameters, such as heart rate. For example, for the first patient, a plot of patient data 1010 may include a waveform 1012 showing monitoring data over time and a current value 1014 for that monitoring data.

The patient data displayed in GUI 1000 may include monitoring compliance data for each patient, determined as explained above with respect to FIGS. 4 and 7. For example, for the first patient, a first plot 1016 shows a rolling average monitoring compliance relative to a target average monitoring compliance over time, with a current average value (e.g., 70%). For the second patient, a first timeline 1018 shows monitoring status over time, with a current average monitoring compliance value (e.g., 80%). For the third patient, a second timeline 1020 shows monitoring status over time, with a current average monitoring compliance value (e.g., 80%). In this way, a care provider may quickly assess monitoring compliance for a plurality of patients at once, which may guide monitoring decisions.

The technical effect of tracking unmonitored time during monitoring of a patient and displaying a patient list including compliance metrics at the display device is to quickly identify if the patient is being effectively monitored and identify areas where monitoring compliance may be improved. By outputting alerts when connection or disconnection delays are detected, signal quality of the monitoring devices is low, time in alarm states is high, etc., care providers may be notified and may quickly attend to the patient, which may improve patient care.

In another representation, a method includes generating a patient list that includes, for each of a plurality of patients, a relative amount of monitored time, a time to monitoring connection, a time to monitoring disconnection, a relative amount of time in an alarm state, and/or a time in an alarm state and outputting the patient list for display on a display device, where for a given patient of the plurality of patients, the relative amount of monitored time is determined over a duration based on an amount of time where data from one or more monitoring devices configured to monitor the given patient was usable for monitoring one or more parameters of the given patient. In a first example of the method, the method further includes, if a relative amount of monitored time for a patient of the plurality of patients is less than a first threshold, outputting a first notification. In a second example of the method, which optionally includes the first example, the method further includes determining, for the given patient, the time to monitoring connection by calculating an amount of elapsed time from when an order to initiate monitoring for the given patient was received until the given patient was connected to the one or more monitoring devices, and if the time to monitoring connection is greater than a second threshold, outputting a second notification. In a third example of the method, which optionally includes one or both of the first and second examples, the patient list further includes, for at least a subset of patients of the plurality of patients, a time to monitoring disconnection. In a fourth example of the method, which optionally includes one or more or each of the first through third examples, the method further includes determining, for the given patient, a time to monitoring disconnection by calculating an amount of elapsed time from when an order to terminate monitoring for the given patient was received until the given patient was disconnected to the one or more monitoring devices. In a fifth example of the method, which optionally includes one or more or each of the first through fourth examples, the relative amount of monitored time is further based on planned unmonitored time and a location of one or more clinicians relative to the given patient.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for patient monitoring, comprising:
   determining, over a duration, a relative amount of monitored time where data from one or more monitoring devices was usable for monitoring one or more parameters of a patient, the relative amount of monitored time being based on an amount of unmonitored time, over the duration, where the data from the one or more monitoring devices was not usable for monitoring the one or more parameters, including time where data from the one or more monitoring devices was not received, based on a signal quality of the data; and
   based on the relative amount of monitored time being less than a threshold amount of monitored time, outputting a first notification.

2. The method of claim 1, further comprising, prior to determining the relative amount of monitored time:
   obtaining a monitoring protocol for the patient that includes one or more target parameters from a set of possible parameters to be monitored;
   identifying one or more current parameters of the patient that are currently being monitored;
   determining whether the one or more current parameters match the one or more target parameters; and
   responsive to determining that the one or more current parameters do not match the one or more target parameters, outputting a second notification.

3. The method of claim 2, wherein determining whether the one or more current parameters match the one or more target parameters comprises determining that the patient is being under-monitored in response to the one or more current parameters including fewer parameters than the one or more target parameters; and
   wherein outputting the second notification comprises outputting the second notification responsive to determining that the patient is being under-monitored.

4. The method of claim 2, wherein determining whether the one or more current parameters match the one or more target parameters comprises determining that the patient is being over-monitored in response to the one or more current parameters including more parameters than the one or more target parameters; and
   wherein outputting the second notification comprises outputting the second notification responsive to determining that the patient is being over-monitored.

5. The method of claim 1, wherein outputting the first notification comprises outputting the first notification for display on a display device.

6. The method of claim 1, further comprising determining, over the duration, a relative amount of alarm time, the relative amount of alarm time including a total amount of time over the duration that any of the one or more monitoring devices were issuing an alarm; and
   if the relative amount of alarm time is greater than a threshold alarm time, outputting a second notification.

7. The method of claim 1, further comprising:
   determining a duration of a connection delay, the duration of the connection delay including an amount of time from when a monitoring order was entered for the patient to when the one or more monitoring devices were actually monitoring the patient; and
   if the duration of the connection delay is greater than a threshold connection delay, outputting a third notification.

8. The method of claim 1, further comprising determining a duration of a disconnect delay, the duration of the disconnect delay including an amount of time from when a monitoring disconnect order was entered for the patient to when the one or more monitoring devices were actually disconnected from the patient; and
if the duration of the disconnect delay is greater than a threshold disconnect delay, outputting a fourth notification.

9. The method of claim 1, wherein determining the relative amount of monitored time comprises:
correcting the amount of unmonitored time by planned unmonitored time and/or based on a location of the one or more clinicians relative to the patient; and
determining the relative amount of monitored time based on the corrected amount of unmonitored time relative to a total length of the duration.

10. The method of claim 1, further comprising generating a patient list that includes a relative amount of monitored time for each of a plurality of patients and outputting the patient list for display on a display device.

11. A method for patient monitoring, comprising:
obtaining a monitoring protocol for a patient including one or more target parameters from a set of possible parameters to be monitored;
receiving data from one or more monitoring devices configured to sense one or more current parameters of the patient;
determining a monitoring condition of the patient based on the monitoring protocol and the data received from the one or more monitoring devices, the determining comprising:
determining that the patient is being under-monitored based on the one or more current parameters being less than the one or more target parameters; and
determining that the patient is being over-monitored based on the one or more current parameters being more than the one or more target parameters; and
outputting an indication of the monitoring condition for display on a display device, the outputting the indication comprising:
based on a determination that the patient is being under-monitored, outputting a notification indicating that the patient is being under-monitored; and
based on a determination that the patient is being over-monitored, outputting a notification indicating that the patient is being over-monitored.

12. The method of claim 11, wherein determining the monitoring condition of the patient comprises determining, over a duration, a relative amount of monitored time where the data from the one or more monitoring devices was usable for monitoring the one or more target parameters of the patient; and
wherein outputting the indication of the monitoring condition comprises outputting a representation of the relative amount of monitored time.

13. The method of claim 11, wherein the monitoring protocol is generated based on one or more of user input from a clinician, department and/or facility guidelines, and medical governing body guidelines.

14. The method of claim 11, wherein determining that the patient is being under-monitored and determining that the patient is being over-monitored comprises determining, over a duration, a relative amount of monitored time where data from the one or more monitoring devices was usable for monitoring the one or more current parameters of the patient, the relative amount of monitored time being based on an amount of unmonitored time.

* * * * *